United States Patent
Oz et al.

(10) Patent No.: US 10,111,600 B2
(45) Date of Patent: *Oct. 30, 2018

(54) SYSTEMS, APPARATUS AND METHODS FOR SENSING FETAL ACTIVITY

(71) Applicant: Nuvo Group Ltd., Tel Aviv (IL)

(72) Inventors: Oren Oz, Modiin (IL); Nathan Intrator, Tel Aviv (IL); Muhammad Mhajna, Umm al Fahem (IL)

(73) Assignee: Nuvo Group Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/205,620

(22) Filed: Jul. 8, 2016

(65) Prior Publication Data

US 2017/0007142 A1   Jan. 12, 2017

Related U.S. Application Data

(63) Continuation of application No. 14/921,489, filed on Oct. 23, 2015, now Pat. No. 9,392,952.

(60) Provisional application No. 62/131,122, filed on Mar. 10, 2015.

(51) Int. Cl.
| A61B 5/0444 | (2006.01) |
| A61B 5/04 | (2006.01) |
| A61B 5/0245 | (2006.01) |
| A61B 5/0452 | (2006.01) |
| A61B 5/00 | (2006.01) |
| A61B 5/024 | (2006.01) |
| A61B 5/0456 | (2006.01) |

(52) U.S. Cl.
CPC ........... *A61B 5/0444* (2013.01); *A61B 5/0245* (2013.01); *A61B 5/02405* (2013.01); *A61B 5/02411* (2013.01); *A61B 5/04014* (2013.01); *A61B 5/04017* (2013.01); *A61B 5/0452* (2013.01); *A61B 5/0456* (2013.01); *A61B 5/04525* (2013.01); *A61B 5/4362* (2013.01); *A61B 5/6823* (2013.01); *A61B 5/7203* (2013.01)

(58) Field of Classification Search
CPC .............. A61B 5/0444; A61B 5/02405; A61B 5/02411; A61B 5/0245; A61B 5/04014; A61B 5/04017; A61B 5/0452; A61B 5/04525; A61B 5/0456; A61B 5/04362; A61B 5/6823; A61B 5/7203
See application file for complete search history.

(56) References Cited

U.S. PATENT DOCUMENTS

| 4,781,200 | A | * | 11/1988 | Baker | ............... | A61B 5/02411 600/483 |
| 4,945,917 | A | * | 8/1990 | Akselrod | ............. | A61B 5/0444 600/509 |
| 5,666,959 | A | * | 9/1997 | Deans | ................. | A61B 5/0444 600/511 |
| 5,749,831 | A | * | 5/1998 | Baker | ...................... | A61B 8/02 600/301 |
| 5,758,654 | A | * | 6/1998 | Burton-Krahn | ...... | A61B 5/7239 600/517 |
| 9,392,952 | B1 | * | 7/2016 | Oz | ........................ | A61B 5/0444 |
| 2008/0146953 | A1 | * | 6/2008 | Kimura | ................ | A61B 5/0444 600/511 |

(Continued)

Primary Examiner — Catherine Voorhees
(74) Attorney, Agent, or Firm — Greenberg Traurig, LLP

(57) ABSTRACT

The invention provides systems and methods for monitoring the wellbeing of a fetus by the non-invasive detection and analysis of fetal cardiac electrical activity data.

20 Claims, 9 Drawing Sheets

(56) References Cited

U.S. PATENT DOCUMENTS

2014/0005988 A1* 1/2014 Brockway .......... H03H 17/0248
 703/2
2016/0022164 A1* 1/2016 Brockway ............ A61B 5/0452
 600/509

* cited by examiner

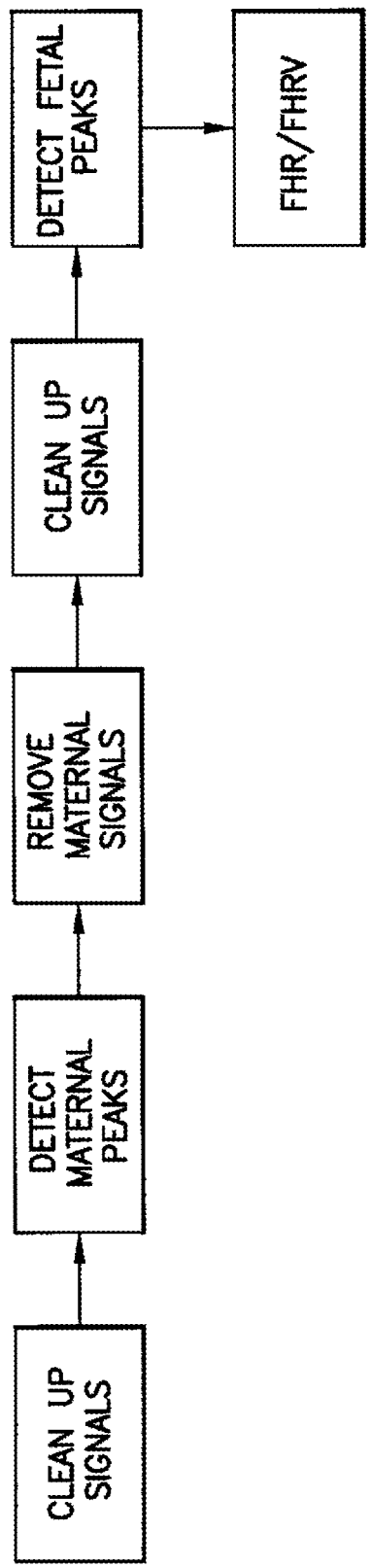

SYSTEMS, APPARATUS AND METHODS FOR SENSING FETAL ACTIVITY

CROSS REFERENCE TO RELATED APPLICATIONS

This application is a continuation of U.S. patent application Ser. No. 14/921,489, filed on Oct. 23, 2015, which claims priority to Provisional Patent Application No. 62/131,122, the contents of which are hereby incorporated by reference in their entirety.

FIELD OF THE INVENTION

The invention relates generally to systems and methods for monitoring the wellbeing of a fetus by the non-invasive detection and analysis of fetal cardiac electrical activity data.

BACKGROUND

Monitoring fetal cardiac can be useful to determine of the health of a fetus during pregnancy.

SUMMARY

In some embodiments, the present invention provides a computer-implemented method, comprising: receiving, by at least one computer processor executing specific programmable instructions configured for the method, raw Electrocardiogram (ECG) signals data from at least one pair of ECG sensors; wherein the at least one pair of ECG sensors are positioned in on an abdomen of a woman carrying a fetus; wherein the raw ECG signals data comprise data representative of a N number of raw ECG signals data (raw N-ECG signals data) which are being acquired in real-time from the at least one pair of ECG sensors; digital signal filtering, by the at least one computer processor, the raw N-ECG signals data to form filtered N-ECG signals data having filtered N-ECG signals; detecting, by the at least one computer processor, maternal heart peaks in each filtered ECG signal in the filtered N-ECG signals data; subtracting, by the at least one computer processor, from each of N-ECG signal of the filtered N-ECG signals data, maternal ECG signal, by utilizing at least one non-linear subtraction procedure to obtain corrected ECG signals data which comprise data representative of a N number of corrected ECG signals, wherein the at least one non-linear subtraction procedure comprises: iteratively performing: i) automatically dividing each ECG signal of N-ECG signals of the filtered N-ECG signals data into a plurality of ECG signal segments, 1) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) automatically modifying each of the second plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being, 2) setting a set of tentative values for a local template for each filtered N-ECG signal segment, 3) utilizing at least one optimization scheme to determine an adaptive template for each filtered N-ECG signal segment based on the local template being matched to the global template within a pre-determined similarity value; and iii) automatically eliminating the modified segments from each of the filtered N-ECG signals, by subtracting the adaptive template from the filtered N-ECG signal thereby generating each corrected ECG signal; extracting, by the at least one computer processor, raw fetal ECG signals data from the filtered N-ECG signals data based on the corrected ECG signals data, wherein the raw fetal ECG signals data comprises a N number of fetal ECG signals (raw N-ECG fetal signals data); processing, by the at least one computer processor, the raw N-ECG fetal signals data to improve a signal-to-noise ratio of the raw N-ECG fetal signals data to form filtered N-ECG fetal signals data; and detecting, by the at least one computer processor, fetal heart peaks in the filtered N-ECG fetal signals data; and calculating, by the at least one computer processor, based on detected fetal heart peaks, at least one of: i) fetal heart rate, ii) fetal heart curve, iii) beat-2-beat fetal heart rate, or iv) fetal heart rate variability; and outputting, by the at least one computer processor, a result of the calculating step.

In some embodiments, the digital signal filtering utilizes at least one of: i) a baseline wander filtering, ii) a power line frequency filtering, iii) a high frequency filtering, or iv) a digital adaptive inverse-median filtering.

In some embodiments, the filtered N-ECG signals data is data which, prior to the detecting the maternal peaks in the filtered N-ECG signals data, has been processed with at least one decomposition technique, wherein the at least one decomposition technique is selected from the group consisting of: a) Singular-Value-Decomposition (SVD), b) Principal-Component-Analysis (PCA), c) Independent-Component-Analysis (ICA), d) Wavelet-Decomposition (CWT), and e) any combination thereof.

In some embodiments, detecting of the maternal heart peaks in each filtered ECG signal in the filtered N-ECG signals data is performed based at least on: i) dividing each filtered ECG signal into a first plurality of ECG signal segments; ii) normalizing a filtered ECG signal in each ECG signal segment; iii) calculating a first derivative of the filtered ECG signal in each ECG signal segment; iv) finding local maternal heart peaks in each ECG signal segment based on determining a zero-crossing of the first derivative; and v) excluding the local maternal heart peaks having at least one of: 1) an absolute value which is less than a pre-determined local peak absolute threshold value; or 2) a distance between the local peaks is less than a pre-determined local peak distance threshold value.

In some embodiments, the pre-determined similarity value is based on an Euclidian distance, wherein the set of parameters is a local minima solution to a non-linear least squares problem solved by at least one of: 1) minimizing a cost function taken as the Euclidian distance; 2) utilizing a Gauss-Newton algorithm; 3) utilizing a Steepest-Descent (Gradient-Descent) algorithm; or 4) utilizing a Levenberg-Marquardt algorithm.

In some embodiments, the processing of the raw N-ECG fetal signals data to improve the signal-to-noise ratio comprises: i) applying a band-pass filter within a range of 15-65 Hz to break the plurality of N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered ECG fetal signals data, comprising a N number of filtered fetal ECG signals (filtered N-ECG fetal signals data).

In some embodiments, the processing of the raw N-ECG fetal signals data to improve the signal-to-noise ratio further comprises at least one of: 1) utilizing a Singular-Value-Decomposition (SVD) technique; or 2) utilizing a Wavelet-Denoising (WD) technique.

In some embodiments, the present invention provides a computer-implemented method, comprising: receiving, by at least one computer processor executing specific programmable instructions configured for the method, raw Electrocardiogram (ECG) signals data from at least one pair of ECG sensors; wherein the at least one pair of ECG sensors are positioned on an abdomen of a woman carrying a fetus; wherein the raw ECG signals data comprise data representative of a N number of raw ECG signals (raw N-ECG signals data) which are being acquired in real-time from the at least one pair of ECG sensors; digital signal filtering, by the at least one computer processor, the raw ECG signals data to form filtered N-ECG signals data having filtered N-ECG signals, wherein the digital signal filtering utilizes at least one of: i) a baseline wander filtering; ii) a power line frequency filtering; iii) a high frequency filtering; or iv) a digital adaptive inverse-median filtering; detecting, by the at least one computer processor, maternal heart peaks in each filtered N-ECG signals data in the filtered N-ECG signals data, by performing at least: i) dividing each filtered ECG signal into a first plurality of ECG signal segments; ii) normalizing a filtered ECG signal in each ECG signal segment; iii) calculating a first derivative of the filtered ECG signal in each ECG signal segment; iv) finding local maternal heart peaks in each ECG signal segment based on determining a zero-crossing of the first derivative; and v) excluding the local maternal heart peaks having at least one of: 1) an absolute value which is less than a pre-determined local peak absolute threshold value; or 2) a distance between the local peaks is less than a pre-determined local peak distance threshold value; subtracting, by the at least one computer processor, from each of filtered N-ECG signal of the filtered N-ECG signals data, the maternal ECG signal, by utilizing at least one non-linear subtraction procedure to obtain corrected N-ECG signals data which comprise data representative of a N number of corrected ECG signals, wherein the at least one non-linear subtraction procedure comprises: iteratively performing: i) automatically dividing each ECG signal of filtered N-ECG signals data into a second plurality of ECG signal segments, 1) wherein each ECG signal segment of the second plurality of ECG signal segments corresponds to a beat interval of a full heartbeat; 2) wherein each beat interval is automatically determined based, at least in part on automatically detecting an onset value and an offset value of such beat interval, and 3) wherein the automatically detecting of the onset value and the offset value of each beat interval is based, at least in part, on: a) a number of maternal peaks detected in each ECG signal, b) changing a sample rate of each ECG signal by an integer number, c) an onset of each P-wave, d) an offset of each T-wave, and e) in-beat segmentation; ii) automatically modifying each of the second plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being; 2) setting a set of tentative values for a local template for each filtered N-ECG signal segment; and utilizing at least one optimization scheme to determine an adaptive template for each filtered N-ECG signal segment based on the local template being matched to the global template within a pre-determined similarity value; and iii) automatically eliminating the modified segments from each the filtered N-ECG signals, by subtracting the adaptive template from the filtered N-ECG signal thereby generating each corrected ECG signal, thereby generating corrected N-ECG signals data; extracting, by the at least one computer processor, raw fetal ECG signals data, by utilizing a Blind-Source-Separation (BSS) algorithm on (1) the filtered N-ECG signals data and (2) the corrected N-ECG signals data, wherein the raw fetal ECG signals data comprises a N number of fetal ECG signals (N-ECG fetal signals); processing, by the at least one computer processor, the raw fetal ECG signals data to improve a signal-to-noise ratio by at least: i) applying a band-pass filter within a range of 15-65 Hz to break the plurality of raw N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered fetal ECG signals data, comprising a N number of filtered fetal ECG signals (filtered N-ECG fetal signals data); detecting, by the at least one computer processor, fetal heart peaks in the filtered N-ECG fetal signals data, by performing at least: i) dividing each filtered N-ECG fetal signal into a first plurality of fetal ECG signal segments; ii) normalizing a filtered fetal ECG signal in each fetal ECG signal segment; iii) calculating a first derivative of the filtered fetal ECG signal in each fetal ECG signal segment; and iv) finding local fetal heart peaks in each fetal ECG signal segment based on determining a zero-crossing of the first derivative; calculating, by the at least one computer processor, based on detected fetal heart peaks, at least one of: i) fetal heart rate, ii) fetal heart curve, iii) beat-2-beat fetal heart rate, or iv) fetal heart rate variability; and outputting, by the at least one computer processor, a result of the calculating step.

In some embodiments, the baseline wander filtering comprises utilizing at least one of: 1) a moving average filter having constant weights, or 2) a moving median filter.

In some embodiments, the power line frequency filtering comprises utilizing at least one of: 1) a band-stop digital filter; or 2) a digital adaptive filter.

In some embodiments, the high frequency filtering comprises utilizing at least one of: 1) a digital low pass filter; 2) a cutoff frequency of at least 70 cycles per second; 3) a smoothing filter; 4) or an edge-preserving filter.

In some embodiments, the edge-preserving filter is one of: a) an adaptive mean filter; or b) an adaptive median filter.

In some embodiments, the digital adaptive inverse-median filtering comprises utilizing an adaptive median filter, having a length to be: 1) a constant value, or 2) adapted depending on at least one local characteristic of the ECG signals data.

In some embodiments, the at least one local characteristic is a duration of at least one of: a) a QRS complex; b) a ST segment; or c) a PR interval.

In some embodiments, the filtered N-ECG signals data is data which, prior to the detecting the maternal peaks in the filtered N-ECG signals data, has been processed with at least one decomposition technique, wherein the at least one decomposition technique is selected from the group consisting of: a) Singular-Value-Decomposition (SVD); b) Principal-Component-Analysis (PCA); c) Independent-Component-Analysis (ICA); d) Wavelet-Decomposition (CWT), and e) any combination thereof.

In some embodiments, the pre-determined similarity value is based on an Euclidian distance, wherein the set of parameters is a local minima solution to a non-linear least squares problem solved by at least one of: 1) minimizing a cost function taken as the Euclidian distance; 2) utilizing a Gauss-Newton algorithm; 3) utilizing a Steepest-Descent (Gradient-Descent) algorithm; or 4) utilizing a Levenberg-Marquardt algorithm.

In some embodiments, the processing of the raw N-ECG fetal signals data to improve the signal-to-noise ratio further comprises at least one of: 1) utilizing a Singular-Value-Decomposition (SVD) technique; or 2) utilizing a Wavelet-Denoising (WD) technique.

In some embodiments, the at least one pair of ECG sensors is selected from the group consisting of: at least one of a wet contact ECG electrode; and at least one dry contact ECG electrode.

In some embodiments, a number of in-beat segments in the in-beat segmentation is based on utilizing at least one of the following: 1) a Divide and Conquer algorithm; or 2) a digital band pass filter.

In some embodiments, the number of in-beat segments is three and are defined as follows: 1) a first in-beat segment defined from the onset value of a particular beat interval to an onset of a QRS complex; 2) a second in-beat segment defined to be the QRS complex; and 3) a third in-beat segment defined from an offset of the QRS complex to the offset value of the particular beat interval.

In some embodiments, the present invention provides a specifically programmed computer system, comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving raw Electrocardiogram (ECG) signals data from at least one pair of ECG sensors; wherein the at least one pair of ECG sensors is positioned in on an abdomen of a woman carrying a fetus; wherein the raw ECG signals data comprise data representative of a N number of raw ECG signals (raw N-ECG signals data) which are being acquired in real-time from the at least one pair of ECG sensors; digital signal filtering the raw ECG signals data to form filtered N-ECG signals data having filtered N-ECG signals; detecting maternal heart peaks in each of the filtered N-ECG signal in the filtered N-ECG signals data; subtracting, from each of the filtered N-ECG signal of the filtered N-ECG signals data, the maternal ECG signal, by utilizing at least one non-linear subtraction procedure to obtain corrected ECG signals data which comprise data representative of a N number of corrected ECG signals (corrected N-ECG signals data), wherein the at least one non-linear subtraction procedure comprises: iteratively performing: i) dividing each filtered N-ECG signal of N-ECG signals of the filtered N-ECG signals data into a second plurality of ECG signal segments) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) modifying each of the plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being; 2) setting a set of tentative values for a local template for each filtered N-ECG signal segment; and 3) utilizing at least one optimization scheme to determine an adaptive template for each filtered N-ECG signal segment based on the local template being matched to the global template within a pre-determined similarity value; and iii) eliminating the modified segments from each of the filtered N-ECG signals, by subtracting the adaptive template from the filtered N-ECG signal thereby generating each corrected ECG signal; extracting raw fetal ECG signals data from the filtered N-ECG signals data based on the corrected ECG signals data, wherein the raw fetal ECG signals data comprises a N number of fetal ECG signals (raw N-ECG fetal signals data); processing the raw N-ECG fetal signals data to improve a signal-to-noise ratio of the N-ECG fetal signals to form filtered N-ECG fetal signals data; detecting fetal heart peaks in the filtered N-ECG fetal signals data; calculating, based on detected fetal heart peaks, at least one of: i) fetal heart rate, ii) fetal heart curve, iii) beat-2-beat fetal heart rate, or iv) fetal heart rate variability; and outputting a result of the calculating operation.

In some embodiments, the present invention provides a specifically programmed computer system, comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving raw Electrocardiogram (ECG) signals data from at least one pair of ECG sensors; wherein the at least one pair of ECG sensors is positioned on an abdomen of a woman carrying a fetus; wherein the raw ECG signals data comprise data representative of a N number of raw ECG signals (raw N-ECG signals data) which are being acquired in real-time from the at least one pair of ECG sensors; digital signal filtering the raw ECG signals data to form filtered N-ECG signals data having filtered N-ECG signals, wherein the digital signal filtering utilizes at least one of: i) a baseline wander filtering; ii) a power line frequency filtering; iii) a high frequency filtering; or iv) a digital adaptive inverse-median filtering; detecting maternal heart peaks in each filtered N-ECG signal in the filtered N-ECG signals data, by performing at least: i) dividing each filtered N-ECG signal into a first plurality of ECG signal segments; ii) normalizing a filtered ECG signal in each ECG signal segment; iii) calculating a first derivative of the filtered ECG signal in each ECG signal segment; iv) finding local maternal heart peaks in each ECG signal segment based on determining a zero-crossing of the first derivative; and v) excluding the local maternal heart peaks having at least one of: 1) an absolute value which is less than a pre-determined local peak absolute threshold value; or 2) a distance between the local peaks is less than a pre-determined local peak distance threshold value; subtracting, from each of the filtered N-ECG signals of the filtered N-ECG signals data, the maternal ECG signal, by utilizing at least one non-linear subtraction procedure to obtain corrected ECG signals data which comprise data representative of a N number of corrected ECG signals (corrected N-ECG signals data), wherein the at least one non-linear subtraction procedure comprises: iteratively performing: i) dividing each ECG signal of the filtered N-ECG signals of the filtered N-ECG signals data into a second plurality of ECG signal segments; 1) wherein each ECG signal segment of the second plurality of ECG signal segments corresponds to a beat interval of a full heartbeat; 2) wherein each beat interval is automatically determined based, at least in part on automatically detecting an onset value and an offset value of such beat interval; and 3) wherein the automatically detecting of the onset value and the offset value of each beat interval is based, at least in part, on: a) a number of maternal peaks detected in each ECG signal; b) changing a sample rate of each ECG signal by an integer number; c) an onset of each P-wave; d) an offset of each T-wave; or e) in-beat segmentation; ii) modifying each of the second plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being; 2) setting a set of tentative values for a local template for each filtered N-ECG signal segment; and 3) utilizing at least one optimization scheme to determine an adaptive template for each filtered N-ECG signal segment based on the local template being matched to the global template within a pre-determined similarity value; and iii) eliminating the modified segments from each the filtered N-ECG signals, by subtracting the adaptive template from the filtered N-ECG signal thereby generating each corrected ECG signal; extracting raw fetal ECG signals data, by utilizing a Blind-Source-Separation (BSS) algorithm on (1) the filtered N-ECG signals data and (2) the corrected N-ECG signals data, wherein the raw fetal ECG signals data comprises a N number of fetal ECG signals (raw N-ECG fetal signals data); processing the raw N-ECG fetal signals data to improve a signal-to-noise ratio by at least: i) applying a band-pass filter within a range of 15-65 Hz to break the plurality of raw N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered fetal ECG signals data, comprising a N number of filtered fetal ECG signals (filtered N-ECG fetal signals data); detecting fetal heart peaks in the filtered N-ECG fetal signals data, by performing at least: i) dividing each filtered fetal N-ECG signal into a first plurality of fetal ECG signal segments; ii) normalizing a filtered fetal ECG signal in each fetal ECG signal segment; iii) calculating a first derivative of the filtered fetal ECG signal in each fetal ECG signal segment; and iv) finding local fetal heart peaks in each fetal ECG signal segment based on determining a zero-crossing of the first derivative; calculating based on detected fetal heart peaks, at least one of: i) fetal heart rate, ii) fetal heart curve, iii) beat-2-beat fetal heart rate, or iv) fetal heart rate variability; and outputting a result of the calculating operation.

BRIEF DESCRIPTION OF THE DRAWINGS

FIG. 2 shows a flow chart of an algorithm used to detect and analyze cardiac electrical activity data according to some embodiments of the present invention.

DETAILED DESCRIPTION

For clarity of disclosure, and not by way of limitation, the detailed description of the invention is divided into the following subsections that describe or illustrate certain features, embodiments or applications of the present invention.

In some embodiments, the present invention provides a system for detecting, recording and analyzing cardiac electrical activity data from a pregnant mother carrying a fetus. In some embodiments, a plurality of ECG sensors is used to record the cardiac electrical activity data. In some embodiments, ECG sensors, comprising electrodes that record cardiac electrical activity data are attached to the abdomen of the pregnant mother. In some embodiments, the ECG sensors are directly attached. In some embodiments, the ECG sensors are incorporated into an article, such as, for example, a belt, a patch, and the like, and the article is worn by, or placed on, the pregnant mother.

The choice of ECG sensors is readily determined by one of ordinary skill in the art. Factors influencing sensor choice include, but are not limited to, the sensitivity of the electrodes, the size of the electrodes, the weight of the electrodes, and the like.

In some embodiments, the ECG sensors are wet-contact electrodes. In some embodiments, the ECG sensors are dry contact electrodes.

Figure 1A:
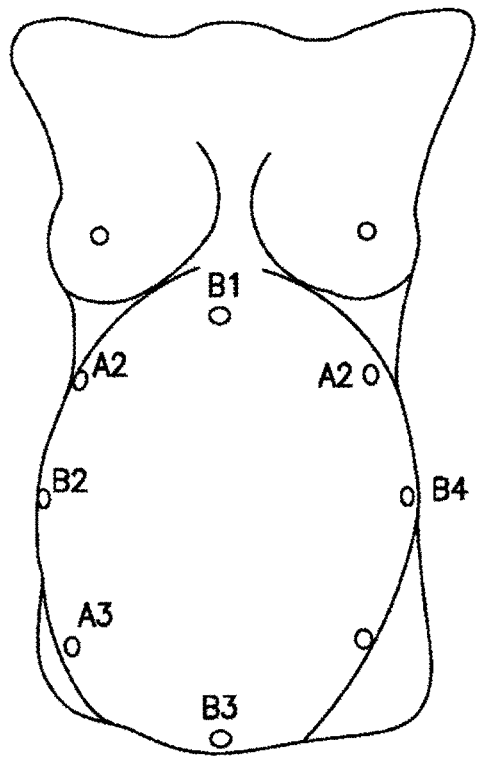
FIGS. 1A-1B shows the positions of the sensor pairs on the abdomen of a pregnant woman according to some embodiments of the present invention. Panel A) shows a front view. Panel B) shows a side view.
Figure 1B:
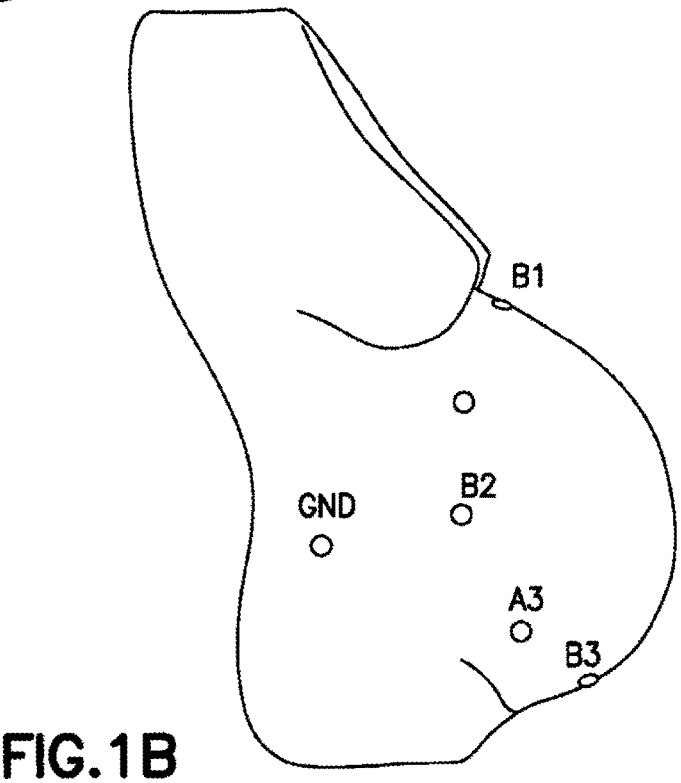

In some embodiments, the arrangement of the ECG sensors provides a system for recording, detecting and analyzing fetal cardiac electrical activity data regardless of sensor position, fetal orientation, fetal movement, or gestational age. In some embodiments, the ECG sensors are attached, or positioned, on the abdomen of the pregnant mother in the configuration shown in FIG. 1. In some embodiments, the ECG sensors are divided into channels comprising a pair of ECG sensors, and cardiac electrical activity data is recorded simultaneously from the channels. In some embodiments, the channels output the acquired signal data, corresponding to the recorded cardiac electrical activity data.

In some embodiments, at least one ECG sensor pair is used to obtain the acquired signal data. In some embodiments, the number of acquired signal data is referred to as "N". In some embodiments, the ability of the system to detect fetal cardiac electrical activity data is increased by increasing the value of N. For example, by way of a non-limiting illustration, in some embodiments, the channels are specified as follows:
 1. B1-B3
 2. B1-B2
 3. B2-B3

4. A1-A4
5. A2-A3
6. A2-A4

In some embodiments, the signal data corresponding to fetal cardiac electrical activity data are extracted from the acquired signal data.

Figure 3:
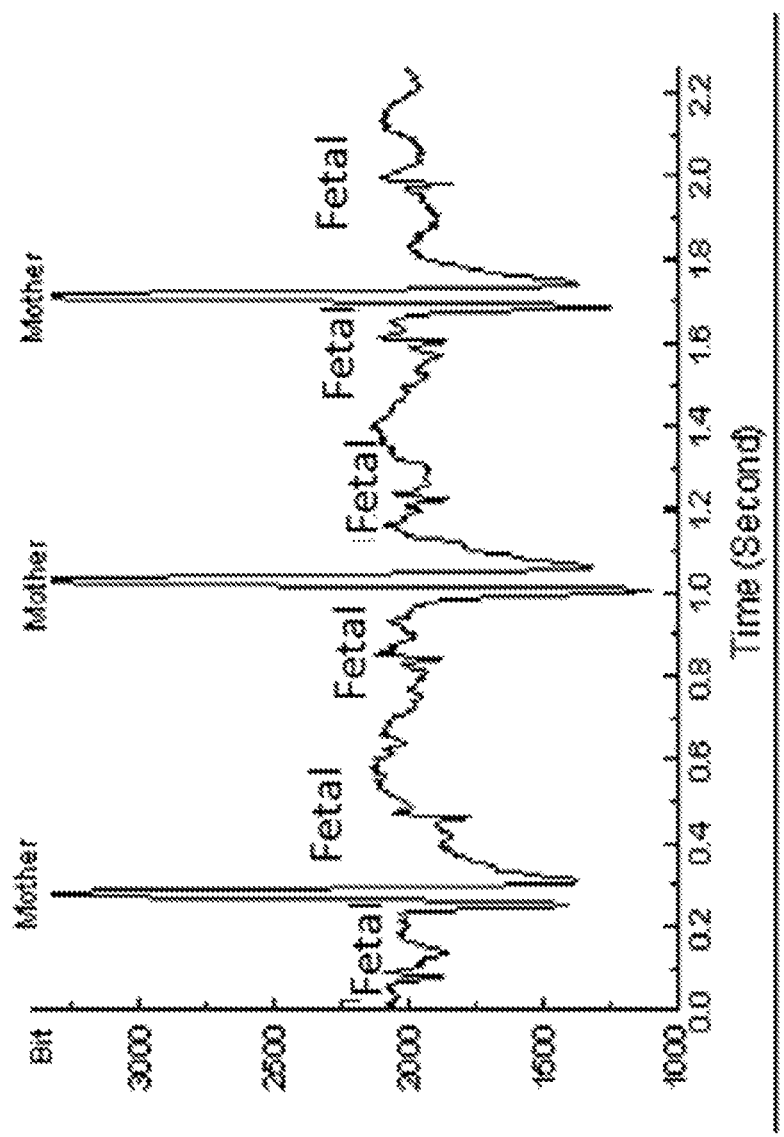
FIG. 3 shows an exemplary recording of cardiac electrical activity data according to some embodiments of the present invention.

Fetal cardiac activity elicits a semi-periodic electrical signal, typically from about 0.1 to 100 Hz. Frequently, signals corresponding to fetal cardiac activity are contaminated with other electrical signals, including maternal cardiac electrical activity. The signal elicited by maternal cardiac activity can be 10-fold greater than the fetal signal corresponding to fetal cardiac activity. See, for example, FIG. 3, showing an exemplary recording of cardiac electrical activity data, showing both maternal and fetal electrical activity combined.

In some embodiments, the fetal cardiac electrical activity data are extracted from the acquired signal data by a method comprising:
 a. obtaining raw N-ECG signals data by recording electrical activity from the abdomen of a pregnant mother carrying a fetus using at least one ECG sensor pair;
 b. applying a set of linear and no-linear mathematical transformations to the raw N-ECG signals data, thereby obtaining transformed/corrected N-ECG signals data; and
 c. finding features in the transformed/corrected N-ECG signals data that correlates to fetal or maternal cardiac electrical activity.

The term "transformations" as used herein refers to linear or non-linear mathematical transformations, which may include, inter alia, digital filtering, mathematical linear or non-linear decomposition, mathematical optimization.

In some embodiments, the fetal cardiac electrical activity data are extracted from the acquired signal data using the algorithm shown in FIG. 2. Using the algorithm shown in FIG. 2, the recorded signal data are pre-processed to remove noise ("Clean up signals"), then the peaks of the maternal cardiac electrical activity are detected (Detect Maternal Peaks"), the maternal cardiac activity signal data is removed ("Remove Maternal Signals"), then the resulting data is processed to remove noise ("Clean up signals"), then the peaks of the fetal cardiac electrical activity are detected (Detect Fetal Peaks"), to detect fetal cardiac activity. The detected fetal activity data is then subsequently analyzed to calculate at least one of the parameters selected from the group consisting of: beat-to-beat fetal heart rate, fetal ECG, average fetal heart rate, and the variability of fetal heart rate.

In some embodiments, the present invention provides a computer-implemented method, comprising: receiving, by at least one computer processor executing specific programmable instructions configured for the method, raw Electrocardiogram (ECG) signals data from at least one pair of ECG sensors; wherein the at least one pair of ECG sensors are positioned in on an abdomen of a woman carrying a fetus; wherein the raw ECG signals data comprise data representative of a N number of raw ECG signals data (raw N-ECG signals data) which are being acquired in real-time from the at least one pair of ECG sensors; digital signal filtering, by the at least one computer processor, the raw N-ECG signals data to form filtered N-ECG signals data having filtered N-ECG signals; detecting, by the at least one computer processor, maternal heart peaks in each filtered ECG signal in the filtered N-ECG signals data; subtracting, by the at least one computer processor, from each of N-ECG signal of the filtered N-ECG signals data, maternal ECG signal, by utilizing at least one non-linear subtraction procedure to obtain corrected ECG signals data which comprise data representative of a N number of corrected ECG signals, wherein the at least one non-linear subtraction procedure comprises: iteratively performing: i) automatically dividing each ECG signal of N-ECG signals of the filtered N-ECG signals data into a plurality of ECG signal segments, 1) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) automatically modifying each of the second plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being, 2) setting a set of tentative values for a local template for each filtered N-ECG signal segment, 3) utilizing at least one optimization scheme to determine an adaptive template for each filtered N-ECG signal segment based on the local template being matched to the global template within a pre-determined similarity value; and iii) automatically eliminating the modified segments from each of the filtered N-ECG signals, by subtracting the adaptive template from the filtered N-ECG signal thereby generating each corrected ECG signal; extracting, by the at least one computer processor, raw fetal ECG signals data from the filtered N-ECG signals data based on the corrected ECG signals data, wherein the raw fetal ECG signals data comprises a N number of fetal ECG signals (raw N-ECG fetal signals data); processing, by the at least one computer processor, the raw N-ECG fetal signals data to improve a signal-to-noise ratio of the raw N-ECG fetal signals data to form filtered N-ECG fetal signals data; and detecting, by the at least one computer processor, fetal heart peaks in the filtered N-ECG fetal signals data; and calculating, by the at least one computer processor, based on detected fetal heart peaks, at least one of: i) fetal heart rate, ii) fetal heart curve, iii) beat-2-beat fetal heart rate, or iv) fetal heart rate variability; and outputting, by the at least one computer processor, a result of the calculating step.

Pre-Processing of the Acquired Signal Data

In some embodiments, the raw N-ECG signals data are preprocessed to remove noise, to generate filtered N-ECG signals data. In some embodiments, the preprocessing comprises applying a digital signaling filter selected from the group consisting of: a baseline wander filter, a power line frequency filter, and a high frequency filter.

In some embodiments, the baseline wander filter is intended to remove low frequency compartments of the recorded signals and enhance fast time varying parts of the signal.

In some embodiments, the baseline wander filter is a moving average filter with constant weights. In some embodiments, the moving average filter with a length of 501 milliseconds is used.

In some embodiments, the baseline wander filter is a moving median filter.

In some embodiments, the powerline frequency filter is intended to remove the power line interference that is picked up by the sensor pairs. In some embodiments, the cut-off frequency of powerline frequency filter is set to the powerline frequency of the geographical area where the system of the present invention is used. For example, if the system is used in Europe, in some embodiments, the cut-off frequency is 49.5 to 50.5 Hz. If the system is used in the USA, in some embodiments, the cut-off frequency is 59.5 to 60.5 Hz.

In some embodiments, the cut-off frequency of the powerline frequency filter is ±10 Hz of the powerline frequency of the geographical area where the system of the present invention is used. In some embodiments, the cut-off frequency of the powerline frequency filter is ±5 Hz of the powerline frequency of the geographical area where the system of the present invention is used.

In some embodiments, a Butterworth type band-step filter with a cut-off frequency of 49.5 to 50.5 Hz whose order is 10th order, 5 sections is used. In some embodiments, a band-stop digital filter is used to attenuate the frequency components of the power line interference. In some embodiments, a digital adaptive filter is used to automatically determine the exact power line frequency before applying the band-stop filter.

In some embodiments, the high frequency filter is intended to remove very high frequency compartments from the acquired signals. In some embodiments, the high frequency filter is a digital low pass filter. In some embodiments, the digital low pass filter is used to attenuates the high frequency compartments of the acquired signals. In some embodiments, the digital low pass filter is a Chebyshev type I low pass filter.

In some embodiments, the cutoff frequency of the low pass filter is set to 70 cycles/second. In some embodiments, the baseline ripple is 0.12 decibels. In some embodiments, the order is 12th order, 6 sections.

In some embodiments, the high frequency filter is a smoothing filter. In some embodiments, the smoothing filter is used to attenuate the high frequency compartments of the raw N-ECG signals data.

In some embodiments, the high frequency filter is an edge preserving filter. In some embodiments, the edge preserving filter is used to remove high frequency noise from the raw N-ECG signals data while preserving valuable information regarding the fetal and maternal ECG signals contained within the raw N-ECG signals data. In some embodiments, the edge preserving filter is an adaptive mean filter. In some embodiments, the edge preserving filter is an adaptive median filter.

In some embodiments, an additional transformation is applied to the filtered N-ECG signals data. In some embodiments, a digital adaptive inverse-median filter is applied to the filtered N-ECG signals data to enhance the maternal ECG peaks.

Figure 4:
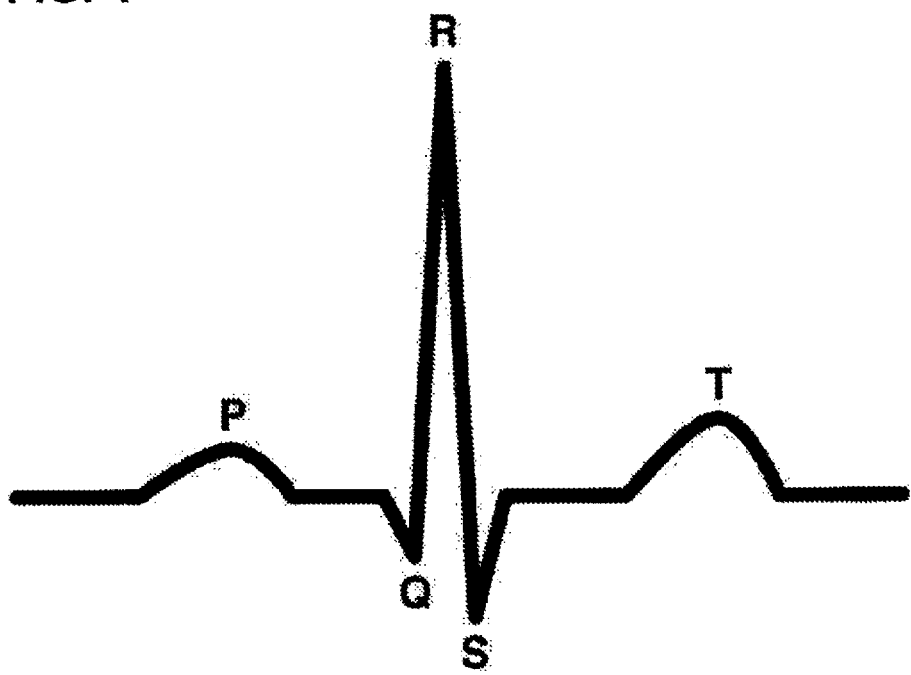
FIG. 4 shows a template maternal electrocardiogram according to some embodiments of the present invention.

The term "maternal ECG peaks" as used herein refers any of the P, Q, R, S or T waves of the electrical activity during a cardiac contraction cycle. FIG. 4 shows a depiction of the electrical activity during a cardiac contraction cycle.

In some embodiments, the additional transformation comprises applying an adaptive median filter to the N filtered N-ECG signals data, and subtracting the result filtered N-ECG signals data.

In some embodiments, the length of the adaptive median filter is selected to be constant. In some embodiments, the length is set to 100 samples.

In some embodiments, the length of the adaptive median filter is adapted depending on the local characteristics of the maternal ECG peaks.

As used herein, the term "local" refers to the signal recorded from a sensor positioned in at a particular location on the abdomen of the pregnant mother.

In some embodiments, the local characteristics are the duration of the QRS segment of the maternal electrical activity during a cardiac contraction cycle.

In some embodiments, the local characteristics are the duration of the ST segment of the maternal electrical activity during a cardiac contraction cycle.

In some embodiments, the local characteristics are the duration of the PR segment of the maternal electrical activity during a cardiac contraction cycle.

In some embodiments, the additional transformation comprises a decomposition to filtered N-ECG signals data to improve the signal to noise ratio. In some embodiments, the decomposition is a singular value decomposition (SVD). In some embodiments, the decomposition is principle component analysis (PCA). In some embodiments, the decomposition is independent component analysis (ICA). In some embodiments, the decomposition is wavelet decomposition (CWT).

In some embodiments, an additional high pass filter is applied to the decomposed filtered N-ECG signals data. In some embodiments, the high pass filter is $5^{th}$ order at 1 Hz. In some embodiments, the decomposed N filtered signal data is examined by preliminary and simple peak detector. In some embodiments, the relative energy of the peaks is calculated (relative to the overall energy of the signal). In some embodiments, the decomposed filtered N-ECG signals data is given a quality score depending on this measure, decomposed filtered N-ECG signals data with a quality score of less than a threshold are excluded and the signals are examined for missing data and NaNs (characters that are non-numerical).

In some embodiments, the quality score is assigned by calculating the relation (energy of peaks)/(Total energy of the filtered N-ECG signal). In some embodiments, the energy of the temporary peaks is calculated by calculating the root mean square of the detected peaks. In some embodiments, the energy of the signal is calculated by calculating the root mean square of the filtered N-ECG signals.

In some embodiments, the threshold is any value from 0.3 to 0.9. In some embodiments, the threshold is 0.8.

Detection of the Portion of the Acquired Signals Corresponding to Maternal Cardiac Activity from the Filtered N-ECG Signals Data and Elimination of the Signals Corresponding to Maternal Cardiac Activity from the Filtered N-ECG Signals Data In some embodiments, maternal heart peaks in each filtered N-ECG signal in the filtered N-ECG signals data are detected and subtracted from each of N-ECG signal of the filtered N-ECG signals data, by utilizing at least one non-linear subtraction procedure to obtain corrected N-ECG signals data which comprise data representative of a N number of corrected ECG signals, wherein the at least one non-linear subtraction procedure comprises: iteratively performing: i) automatically dividing each ECG signal of N-ECG signals of the filtered N-ECG signals data into a plurality of ECG signal segments, 1) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) automatically modifying each of the second plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being, 2) setting a set of tentative values for a local template for each filtered N-ECG signal segment, 3) utilizing at least one optimization scheme to determine an adaptive template for each filtered N-ECG signal segment based on the local template being matched to the global template within a pre-determined similarity value; and iii) automatically eliminating the modified segments from each of the filtered N-ECG signals, by subtracting the adaptive template from the filtered N-ECG signal thereby generating each corrected ECG signal.

Figure 7:
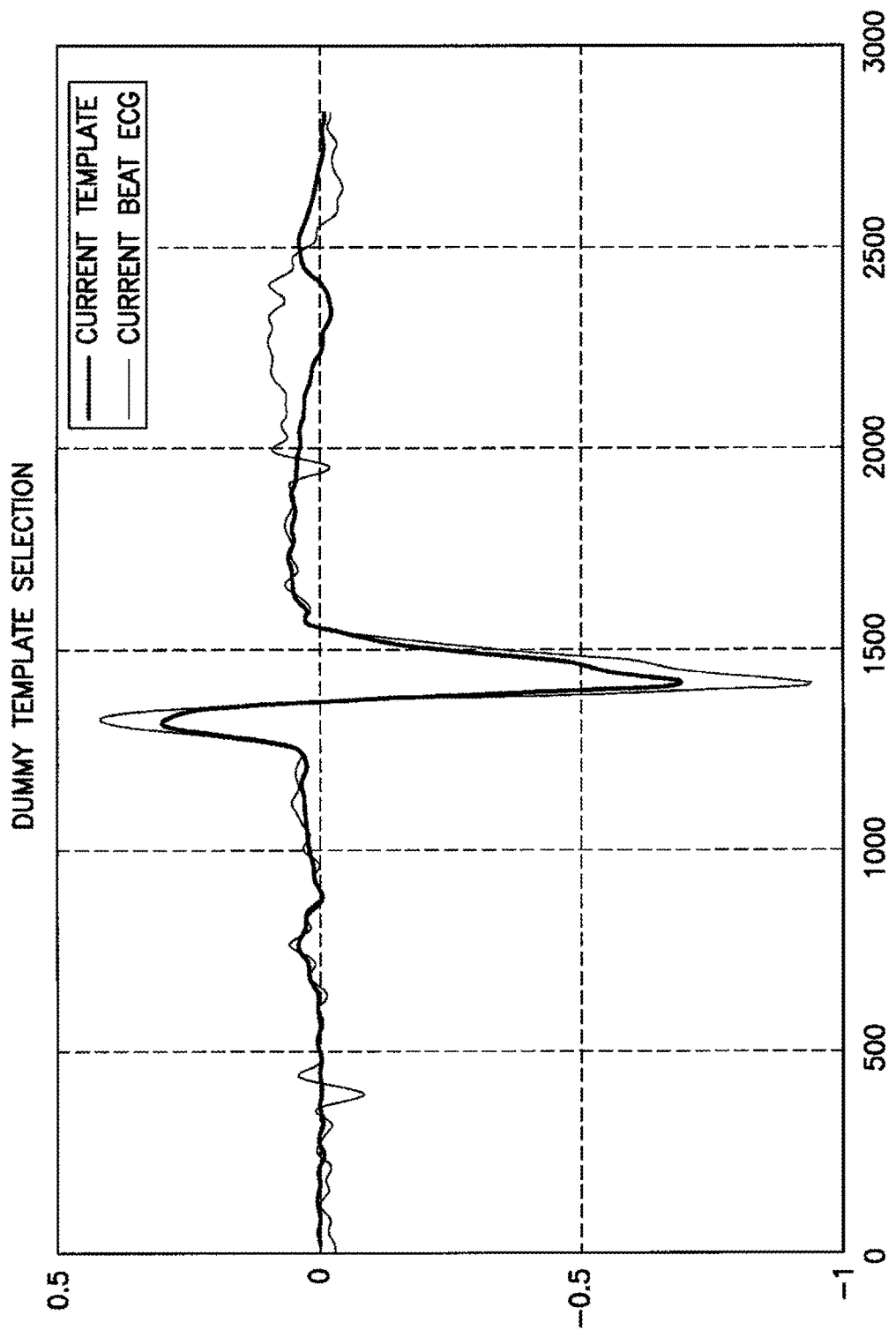
FIG. 7 shows an overlay of a template maternal electrocardiogram over a single maternal heart beat according to some embodiments of the present invention.
Figure 8:
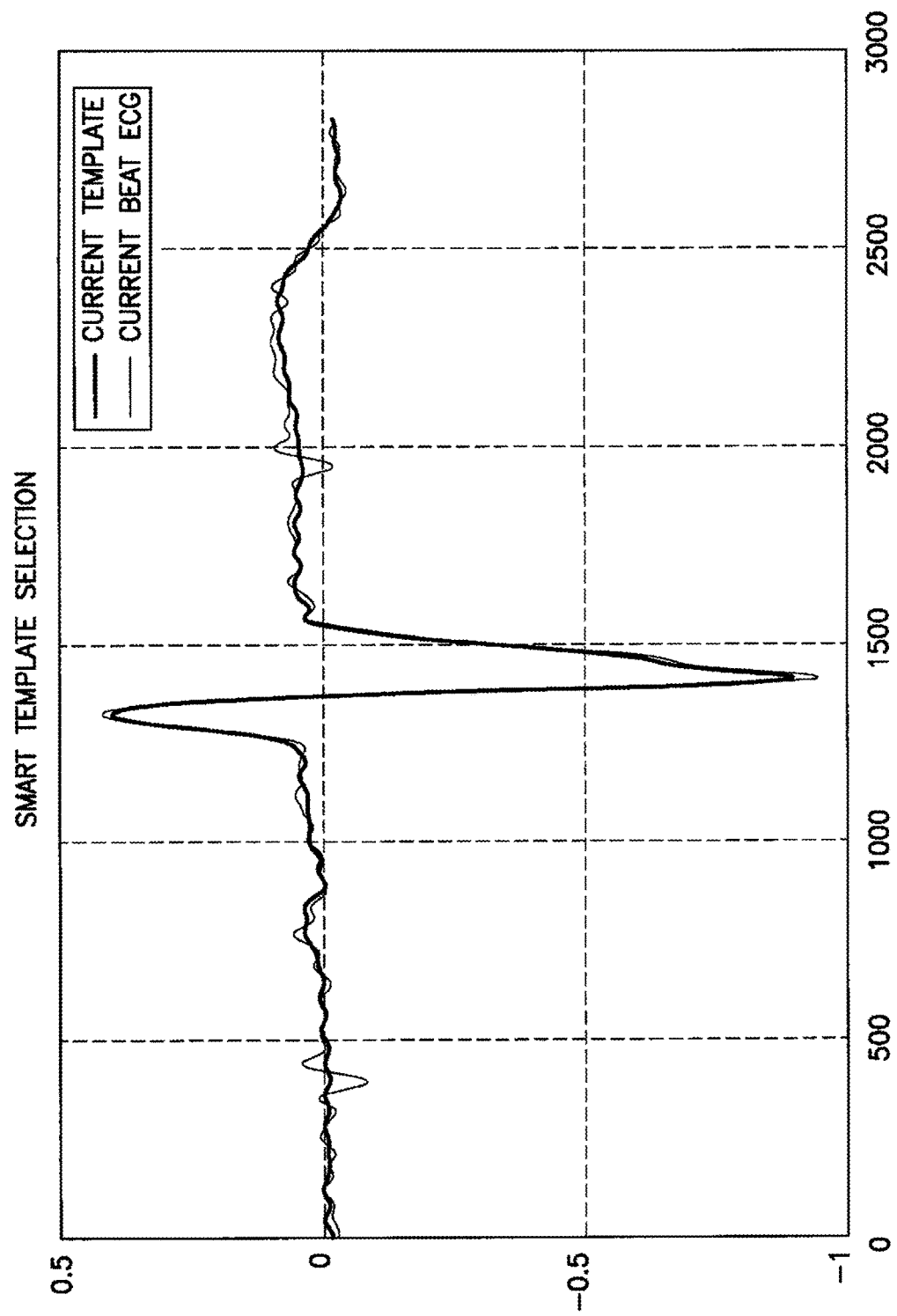
FIG. 8 shows an overlay of a template maternal electrocardiogram over a single maternal heart beat according to some embodiments of the present invention.

Examples of adaptive templates according to some embodiments of the present invention are shown in FIGS. 4, 7 and 8.

In some embodiments, detecting of the maternal heart peaks in each filtered ECG signal in the filtered N-ECG signals data is performed based at least on: i) dividing each filtered ECG signal into a first plurality of ECG signal segments; ii) normalizing a filtered ECG signal in each ECG signal segment; iii) calculating a first derivative of the filtered ECG signal in each ECG signal segment; iv) finding local maternal heart peaks in each ECG signal segment based on determining a zero-crossing of the first derivative; and v) excluding the local maternal heart peaks having at least one of: 1) an absolute value which is less than a pre-determined local peak absolute threshold value; or 2) a distance between the local peaks is less than a pre-determined local peak distance threshold value.

In some embodiments, the pre-determined similarity value is based on an Euclidian distance, wherein the set of parameters is a local minima solution to a non-linear least squares problem solved by at least one of: 1) minimizing a cost function taken as the Euclidian distance; 2) utilizing a Gauss-Newton algorithm; 3) utilizing a Steepest-Descent (Gradient-Descent) algorithm; or 4) utilizing a Levenberg-Marquardt algorithm.

In some embodiments, the length of each segment is set at 10 seconds.

In some embodiments, the length of each segment is selected automatically depending on the length of the recording.

In some embodiments, the signal data in each segment is normalized by the absolute maximum value of the signal data. In some embodiments, the signal data in each segment is normalized by the absolute non-zero minimum value of the signal data.

In some embodiments, a first order forward derivative is used. In some embodiments, a first order central derivative is used.

In some embodiments, the threshold is selected to be a constant value of 0.3.

In some embodiments, the threshold is selected depending on the local characteristics of the signal data. In some embodiments, the local characteristic of the signal is the median value of the signal data or any multiplication of this value. In some embodiments, the local characteristic of the signal is the mean value of the signal data or any multiplication of this value.

In some embodiments, the threshold on the distance is selected to be 100 samples.

In some embodiments, the local characteristics of the signal can be the maximum predicted RR internal or any multiple of this value.

In some embodiments, a "peaks array" is generated from the filtered N-ECG signals data. In some embodiments, the peak array comprises the number of detected peaks for each of the segments of the filtered N-ECG signals data.

In some embodiments, clustering is performed on the peaks array. In some embodiments, k-means clustering is used to group the peaks into a number of clusters. In some embodiments, k-medoids clustering is used to group the peaks into a number of clusters.

In some embodiments, the number of clusters for the clustering is set to be three. In some embodiments, the number of clusters for the clustering is selected automatically depending on the characteristics of the processed N filtered signal data.

In some embodiments, the clustering is used to exclude outliers. In some embodiments, outliers are peaks that have anomalous characteristics.

In some embodiments, the characteristic is the distance between a peak and its neighboring peaks. In some embodiments, the characteristic is the amplitude of the peak.

In some embodiments, a new peak array is constructed after the exclusion of the anomalous peaks.

In some embodiments, the new peak array is further analyzed and the peaks are scored depending on the signal to noise ratio of the filtered N-ECG signals data.

In some embodiments, the signal to noise ratio score is calculated by calculating the relative energy of the QRS complexes from the overall energy of the processed N filtered signal data.

In some embodiments, the detected peaks for each of the filtered N-ECG signals data are fused for a more robust detection. In some embodiments, the fusion of the detected peaks is done using the scores given for each of the peaks of the filtered N-ECG signals data.

In some embodiments, a global array of peaks is defined using the fused peaks.

In some embodiments, the peaks of each of the filtered N-ECG signals data is redetected and the positions are refined using the global peaks array. In some embodiments, the global peak array is constructed based on the best lead with corrections made using the peaks from the other leads and the global peaks array is examined using physiological measures, such as, for example, RR intervals, HR, HRV).

In some embodiments, after the peaks have been defined, the filtered N-ECG signals data is further transformed to eliminate the signals corresponding to maternal cardiac activity. In some embodiments, the transformations/corrections include applying non-linear subtraction to the filtered N-ECG signals data. In some embodiments, the remaining data comprises signal data corresponding to fetal cardiac activity and noise.

In some embodiments of the invention, the non-linear subtraction procedure is applied separately for each one of the processed N filtered signal data. In some embodiments, the non-linear subtraction procedure is applied to all of the processed N filtered signal data in series, in any order. In some embodiments, the non-linear subtraction procedure is applied to all of the processed N filtered signal data simultaneously.

In some embodiments, the non-linear subtraction comprises: dividing the processed N filtered signal data into a large number of segments; modifying each of the segments, separately or jointly, using an inverse optimization scheme; and eliminating the modified segments from the original processed N filtered signal data, thereby obtaining N raw fetal signal data.

The term 'segmentation', as used herein, refers to the division of the processed N filtered signal data into any given number of segments.

In some embodiments, the number of segments is set to be a function of the number of the detected maternal peaks. In some embodiments, the function is the identity function so that the number of segments equals the number of the detected maternal peaks, in which case, each segment is a full heartbeat.

In some embodiments, a beat interval is defined. The term 'beat interval' used hereinafter refers the time interval of a single maternal heart beat.

In some embodiments, the beat interval is taken to be constant and is defined as 500 milliseconds before the R-peak position and 500 milliseconds after the R-peak position.

In some embodiments, the beat interval is detected automatically by detecting the beat onset and beat offset of each beat. Thus, the beat interval depends on the local heart rate value and a more accurate segmentation of the ECG signal is achieved.

In some embodiments, the beat interval onset is defined as the onset (i.e. starting point in time) of the P-wave.

In some embodiments, the beat interval offset is defined as the offset (i.e. end point in time) of the T wave.

In some embodiments, the beat interval onset for the current beat is defined as half the way, in time, between the previous beat and the current beat.

In some embodiments, the beat interval offset for the current beat is defined as half the way, in time, between the current beat and the next beat.

In some embodiments, a second segmentation step is performed on the result of the previous segmentation. The product of this segmenting step is referred to as 'in-beat segments'.

In some embodiments, the number of in-beat segments is selected to be any integer number between one and the number of time samples in the current beat. By way of non-limiting example, the number of in-beat segment can be three.

In some embodiments, an automatic procedure is performed to detect the optimal number of in-beat segments. In some embodiments, the automatic procedure comprises using a Divide and Conquer algorithm, wherein each segment is divided into two equal sub-segments. If the energy content of a sub-segment exceeds a pre-defined relative threshold, the sub-segment itself is divided into two sub-segments and so on recursively. The stop criterion can be reaching a minimum length of sub-segment, reaching a maximum number of segments or dividing into sub-segments such that all of them meet the energy threshold criterion.

In certain embodiments, the entropy measure is used to divide the segment into sub-segments. In this case, the entropy of each segment is minimized.

In some embodiments, the result of the in-beat segmentation is the following seven segments:

1. The isoelectric line from the beat onset to the onset of the P wave;
2. The P wave;
3. The isoelectric line from offset of the P wave to the onset of the QRS complex;
4. The QRS complex;
5. The isoelectric line from the offset of the QRS complex to the onset of the T wave;
6. The T wave; and
7. The isoelectric line from the offset of the T wave to the beat offset.

In some embodiments, the majority of the energy of the filtered N-ECG signals data is in the QRS complex. Thus, in some embodiments, the in-beat segments a the following three in-beat segments:

1. From the beat onset to the onset of the QRS complex;
2. The QRS complex; and
3. From the offset of the QRS complex to the beat offset.

In some embodiments, the onset and offset of the QRS complex, for each of the beats in the ECG signal, are automatically detected using a dedicated method comprising: applying a digital band pass filter to the filtered N-ECG signals data; calculating the curve length transform of the filtered N-ECG signals data; selecting the values of the data that are higher than a threshold; calculating the first derivative of the transformed data; finding the positive transitions and negative transitions in the derivative data; finding pairs of the positive-and-negative transition such that the distance between them, in time samples, is higher than a pre-selected threshold; setting the onset of the QRS complex as the position, in time, of the positive transition from the selected pair; and setting the offset of the QRS complex as the position in time of the negative transition from the selected pair.

In some embodiments, the cutoff frequencies of the band pass filter are set to be 5 and 20 cycles/sec for the lower and upper frequencies respectively.

In some embodiments, the threshold is set to be a constant value of 0.3. In some embodiments, the threshold value is calculated automatically depending of the local characteristics of the data after the curve length transform. In some embodiments, the local characteristic of the data is the mean value of the transformed data.

In some embodiments, the segmentation also comprises an additional complementary transformation that comprises changing the sample rate of the signal by an integer value. In some embodiments, the additional complementary transformation reduces the variability of the resulting raw N-ECG fetal signals data caused by the fine positions of the onsets and offsets of the selected segments.

In some embodiments the sample rate is decreased by a factor of 4 to decrease the calculation time. Alternatively, in certain embodiments, the sample rate is increased by a factor of 4.

In some embodiments, increasing the sample rate is done using interpolation. In some embodiments, increasing the sample rate is done by zero padding the data and then applying a set of low pass FIR filters.

In some embodiments, changing the sample rate of the signals is done before the segmentation procedure. In some embodiments, changing the sample rate is done after the segmentation. In these embodiments, the selected onsets and offsets of the different segments are refined depending on the signals after changing the sample rate.

In some embodiments, the segmentation is updated depending on the convergence of the iterative methods in the next steps described hereinafter.

In some embodiments, the selected segments are modified using a nonlinear parametric transformation in which the values of a predefined set of parameters are changed according to some criterion.

In some embodiments, the values of a predefined set of parameters are determined and modified according to a method comprising: defining reference vectors as, for each filtered N-ECG signals data, the ECG signal and its segments (called 'measured potentials' hereinafter); and finding the values of the set of parameters that provide a good fit to results of the measured potentials.

A "good fit" occurs when the difference between the adapted template and the measured potentials is very small. In one embodiment, very small is defined to be $10^{-5}$ or smaller. In other embodiments, "very small" is defined as $10^{-6}$ or smaller or $10^{-4}$ or smaller or $10^{-7}$ or smaller or other exponents of 10 or other numbers.

In some embodiments, the difference between the adapted template and the measured potentials is the L2 norm of the element-by-element subtraction between the two vectors.

In some embodiments, the values of a predefined set of parameters also include parameters that change the amplitude of a time signal.

In some embodiments, an iterative scheme is used to determine the values of the set of the parameters, comprising: selecting starting conditions; assigning tentative values to the set of parameters; adapting the templates using the set of parameters; comparing the adapted templates to the measured potentials; checking if a stop criterion is reached; updating the values of the set of parameters if none of the stop criteria are reached, and repeating steps steps (c), (d), (e) and (f). In some embodiments, if a stop criterion is reached, the iterative procedure is terminated and the current set of parameters is deemed the optimal solution of the optimization problem.

In some embodiments, the starting conditions are set to be the ECG templates. In some embodiments, two templates are defined: The first is a global template that is defined for every ECG beat (see, for example, FIG. 7), wherein the template is calculated as a weighted average of M beats. In some embodiments, M is an integer number between 2 and the total number of beats in the ECG signal. In some embodiments, the weights used in the weighted average are equal yielding a normal averaging. In some embodiments, the M beats fulfill the condition that the correlation coefficient between each of the beats should be higher than a threshold. In certain embodiments, the threshold is set to be 0.98. In some embodiments, before the averaging, the beats are shifted and fine aligned using the exact position of the R-wave, the QRS onset and the QRS offset. In some embodiments, the alignment procedure is done using the cross correlation function. In Some embodiments, the M beats fulfill the condition that relation between the energy of the template, defined as an average of these beats, and the energy of the current ECG beat is bounded close to 1. However, in some embodiments, the relation between the energy of the template and the energy of the current ECG beat is higher than 1 by a small value or lower than 1 by a small value.

The second is a local template that is defined for each of the sub-segments in the current beat (see, for example, FIG. 8). In some embodiments, the template is calculated as the average of the sub-segments in the M-selected peaks. In some embodiments, the beats are selected to fulfill the conditions that the local heart rate is similar to the local heart rate for the current beat. By means of a non-limiting example, the heart rate values are close by a factor of 1.5.

In some embodiments, the tentative values are set to random numbers. In some embodiments, the tentative values are set to be constant numbers; by means of a non-limiting example, they are set to be 1.

In some embodiments, the tentative values are saved between different executions of the algorithm and used if available.

In some embodiments, the different templates are adapted separately depending on the appropriate parameters that are assigned to the templates. In some embodiments, the templates are scaled by multiplying the templates vectors with the appropriate set of parameters. In some embodiments, the templates are shifted in time using the appropriate set of parameters.

In some embodiments, the Euclidian distance is used to compare the two sets of vectors; the adapted templates and the measured potentials from the processed N filtered signal data. In some embodiments, the cost function is defined as the error energy function.

In some embodiments, the city-block measure is used to compare the adapted templates to the measured potentials.

In some embodiments, the cross correlation function is used to compare the adapted templates and measured potentials. In some embodiments, a "good fit" is a correlation of 0.95 or greater.

In some embodiments, a maximum number of iterations is used as a stop criterion.

In some embodiments, in the case of using the Euclidian distance as a similarity measure, the value of the error energy function at a specific iteration is used as a stop criterion. In some embodiments, if the error energy becomes lower than a threshold, the stop criterion is reached.

In certain embodiments, the threshold is set to be constant. By means of a non-limiting example, it is set to be $10^{-5}$.

In some embodiments, the threshold is calculated depending on the characteristics of the iterative procedure. For example, in some embodiments, the characteristics of the iterative procedure is the maximum number of allowed iterations; in other embodiments, the characteristics of the iterative procedure is the used cost function, for example the Euclidian distance function; and still other embodiments, the characteristics of the iterative procedure is the number of time samples in the templates.

In some embodiments, an improvement measure is used as a stop criterion.

In some embodiments, the change in the set of parameters is used as an improvement measure. In some embodiments, if the values of the set of parameters does not change, or change slightly, the stop criterion is fulfilled.

In some embodiments, the change in the value of the cost function, e.g. the error energy function, is used as an improvement measure.

In some embodiments, if a stop criterion is reached, an optimization scheme is applied to update the values of the set of parameters.

In some embodiments, when using the Euclidian distance as a similarity measure, the optimization problem becomes a non-linear least squares problem. In some embodiments, the solution of this problem gives the optimal set of parameters that minimizes the cost function taken as the Euclidian distance.

In some embodiments, Gauss-Newton algorithm is used to solve the non-linear least squares problem.

In some embodiments, the Steepest-Descent (Gradient-Descent) method is used to solve the non-linear least squares problem.

In some embodiments, the Levenberg-Marquardt algorithm is used to solve the non-linear least squares problem. In these embodiments, the problem becomes a damped least squares problem. Levenberg-Marquardt algorithm is a method, which interpolates between the Gradient-Descent and Gauss-Newton algorithm taking advantage of both methods to increase the convergence accuracy and decrease the convergence time.

In some embodiments, Gradient-Descent, Gauss-Newton algorithm and Levenberg-Marquardt algorithm, are iterative methods that are repeated a number of times, potentially, bringing the Euclidian distance (the error energy function) to a local minima.

In some embodiments, updating the set of parameters is performed using the relation:

$$P_{k+1}=P_k-[\mathcal{J}_k^T\mathcal{J}_k+\lambda_i \text{diag}(\mathcal{J}_k^T\mathcal{J}_k)]^{-1}*\mathcal{J}_k^T[\phi_c(P_k)-\phi_m]$$

Where $P_k$ is the set of parameters at the $k^{th}$ iteration; and $\phi_c$ ($P_k$) is the adapted version of the templates for the $P_k$ parameters; and $\lambda_i$ is the damping parameter in the Levenberg-Marquardt algorithm; and $\phi_m$ is the measured potentials (measured ECG signals); and $\mathcal{J}_k$ is the Jacobian matrix calculated for the set of parameters $P_k$ by altering the values of the parameters; and $\text{diag}(\mathcal{J}_k^T\mathcal{J}_k)$ is the diagonal of the approximated Hessian matrix.

In some embodiments, eliminating the modified segments from the N raw signal data is achieved by subtracting the adapted templates from the measured potentials. In some embodiments, the subtraction results in N raw fetal signal data. In some embodiments, the N raw fetal signal data comprises noise and fetal cardiac electrical activity data.

Figure 5:
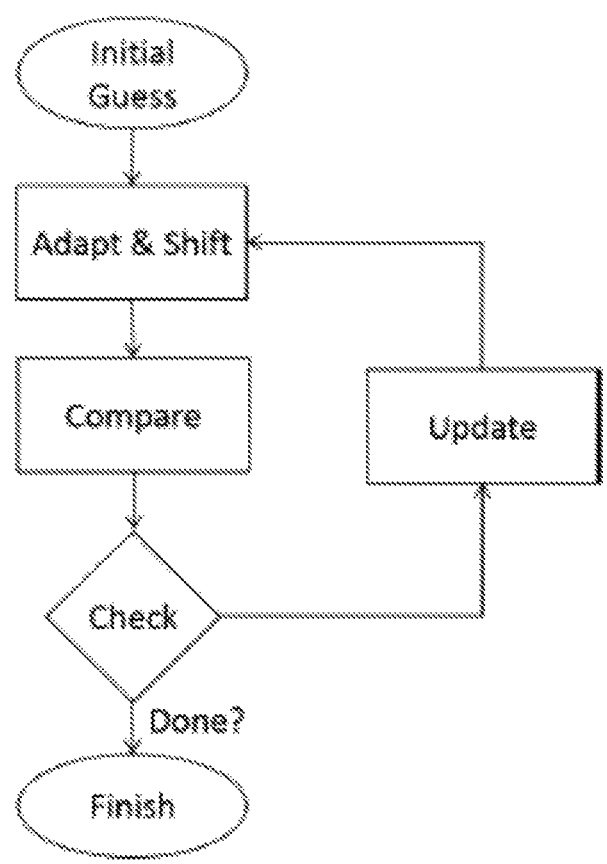
FIG. 5 shows a flow chart of an algorithm used to perform maternal cardiac activity elimination according to some embodiments of the present invention.

In some embodiments, maternal cardiac activity is eliminated using the algorithm shown in FIG. 5.

Figure 6:
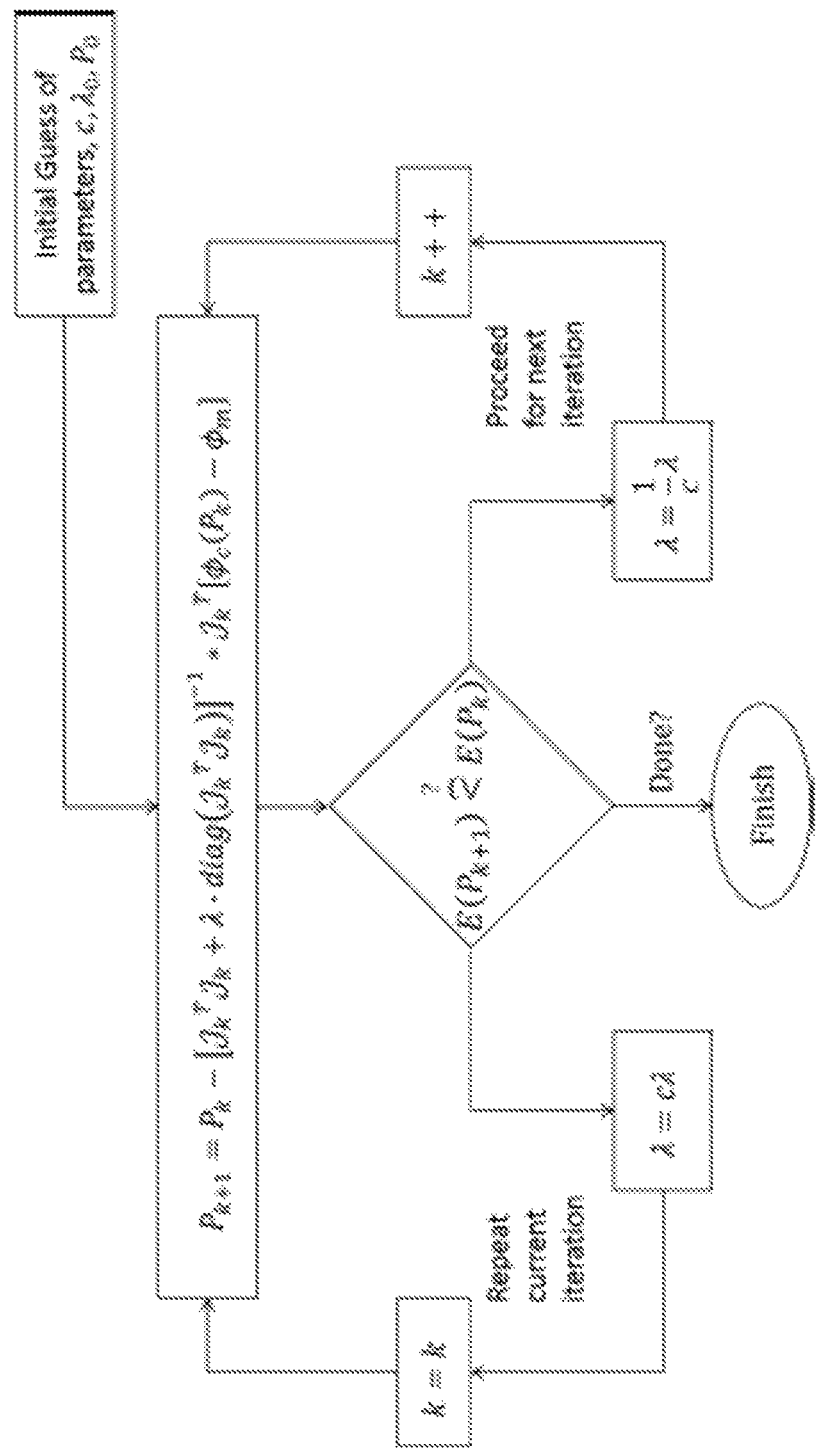
FIG. 6 shows a flow chart of an algorithm used to perform maternal cardiac activity elimination according to some embodiments of the present invention.

In some embodiments, maternal cardiac activity is eliminated using the algorithm shown in FIG. 6.

Figure 9:
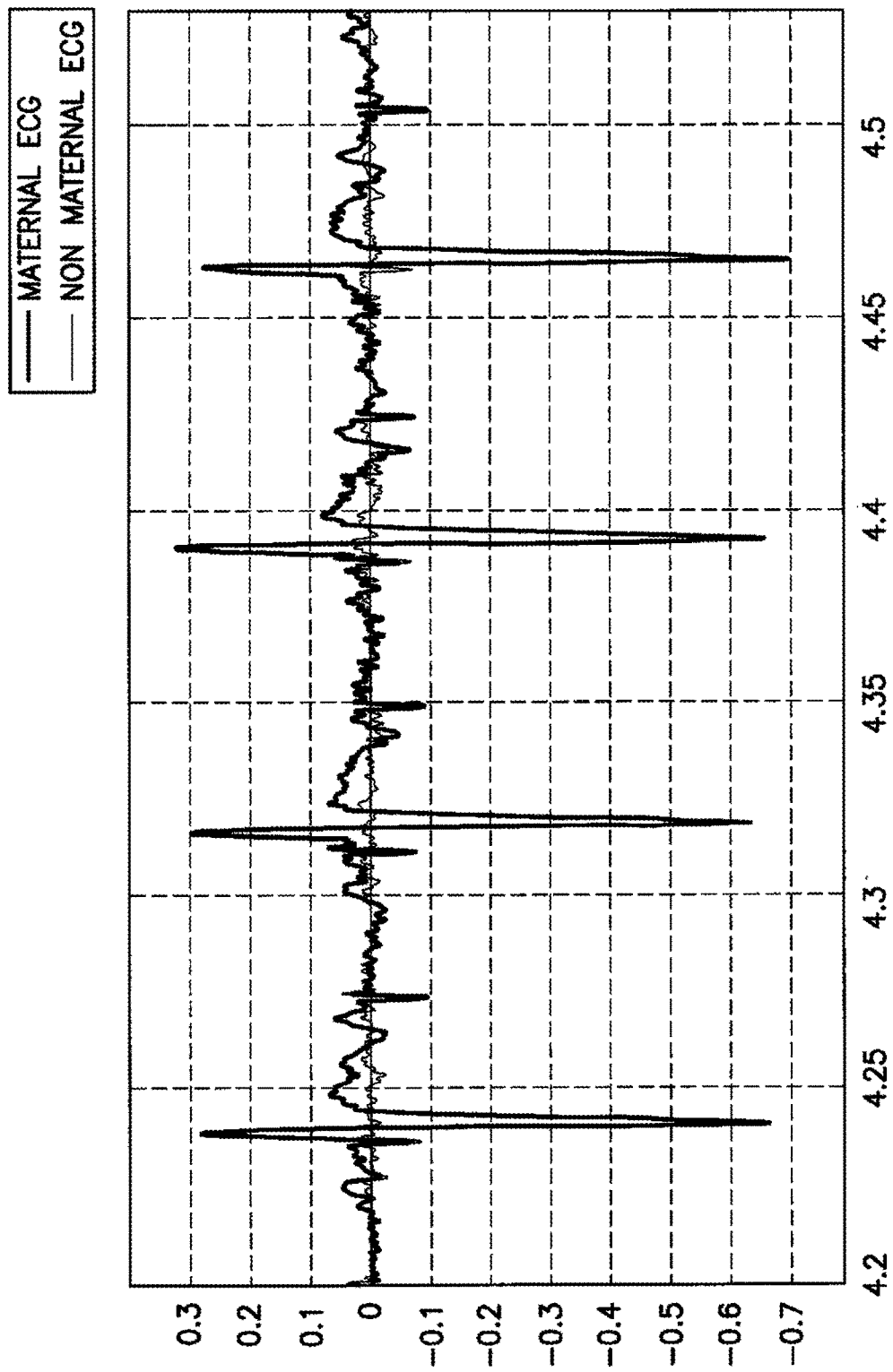
FIG. 9 shows the result of maternal ECG elimination of according to some embodiments of the present invention.

A representative result of maternal ECG elimination according to some embodiments of the present invention is shown in FIG. 9.

Extraction of the Fetal Cardiac Electrical Activity Data and Detecting Fetal Cardiac Electrical Activity Data In some embodiments, raw fetal ECG signals data is extracted and analyzed by utilizing a Blind-Source-Separation (BSS) algorithm on (1) the filtered N-ECG signals data and (2) the corrected N-ECG signals data, wherein the raw fetal ECG signals data comprises a N number of fetal ECG signals (N-ECG fetal signals); processing, by the at least one computer processor, the raw fetal ECG signals data to improve a signal-to-noise ratio by at least: i) applying a band-pass filter within a range of 15-65 Hz to break the plurality of raw N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered fetal ECG signals data, comprising a N number of filtered fetal ECG signals (filtered N-ECG fetal signals data); detecting, by the at least one computer processor, fetal heart peaks in the filtered N-ECG fetal signals data, by performing at least: i) dividing each filtered N-ECG fetal signal into a first plurality of fetal ECG signal segments; ii) normalizing a filtered fetal ECG signal in each fetal ECG signal segment; iii) calculating a first derivative of the filtered fetal ECG signal in each fetal ECG signal segment; and iv) finding local fetal heart peaks in each fetal ECG signal segment based on determining a zero-crossing of the first derivative; calculating, by the at least one computer processor, based on detected fetal heart peaks, at least one of: i) fetal heart rate, ii) fetal heart curve, iii) beat-2-beat fetal heart rate, or iv) fetal heart rate variability; and outputting, by the at least one computer processor, a result of the calculating step.

In some embodiments, the processing of the raw N-ECG fetal signals data to improve the signal-to-noise ratio comprises: i) applying a band-pass filter within a range of 15-65 Hz to break the plurality of N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered ECG fetal signals data, comprising a N number of filtered fetal ECG signals (filtered N-ECG fetal signals data).

In some embodiments, the processing of the raw N-ECG fetal signals data to improve the signal-to-noise ratio comprises: i) applying a band-pass filter within a range of 1-70 Hz to break the plurality of N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered ECG fetal signals data, comprising a N number of filtered fetal ECG signals (filtered N-ECG fetal signals data).

In some embodiments, the processing of the raw N-ECG fetal signals data to improve the signal-to-noise ratio comprises: i) applying a band-pass filter within a range of 5-70 Hz to break the plurality of N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered ECG fetal signals data, comprising a N number of filtered fetal ECG signals (filtered N-ECG fetal signals data).

In some embodiments, the processing of the raw N-ECG fetal signals data to improve the signal-to-noise ratio comprises: i) applying a band-pass filter within a range of 10-70 Hz to break the plurality of N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered ECG fetal signals data, comprising a N number of filtered fetal ECG signals (filtered N-ECG fetal signals data).

In some embodiments, the processing of the raw N-ECG fetal signals data to improve the signal-to-noise ratio comprises: i) applying a band-pass filter within a range of 1-65 Hz to break the plurality of N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered ECG fetal signals data, comprising a N number of filtered fetal ECG signals (filtered N-ECG fetal signals data).

In some embodiments, the processing of the raw N-ECG fetal signals data to improve the signal-to-noise ratio further comprises at least one of: 1) utilizing a Singular-Value-Decomposition (SVD) technique; or 2) utilizing a Wavelet-Denoising (WD) technique.

In some embodiments, all of the raw N-ECG signals data are used in the BSS procedure so that the BSS procedure is applied to 2N signals. In other embodiments, only part of the raw N-ECG signals data is used in the BSS procedure so that the BSS procedure is applied to between N+1 signals and less than 2N signals.

In some embodiments, Principal Component Analysis (PCA) is used as the BSS method. In some embodiments, Independent Component Analysis (ICA) is used as the BSS method.

In some embodiments, the results of the BSS procedure is further analyzed to improve the signal to noise ratio of the signals. In some embodiments, the further analysis includes a band-pass filter in the range of 15-65 cycle/second. In some embodiments, the further analysis includes applying Singular-Value-Decomposition (SVD). In some embodiments, the further analysis includes applying Wavelet-Denoising.

In some embodiments, the further analysis includes applying 'peak-2-mean' transformation, which in some versions is in a separate software module, that comprises:

a. using a moving window ($win$) to calculate the relation: $\frac{\max(\text{Signal}[win])}{\text{mean}(\text{Signal}[win])}$;

and
b. calculating the 1st derivative of the result of step a; and
c. finding the zero crossing to find peaks taking the negative part of the derivative; and
d. finding the peaks in the previous result and cluster them based on the difference between them. Identify the best group as the group with the maximum score defined as: SCR=n/RMS where n is the number of peaks in each cluster and RMS is the energy of the derivative of the distances between the peaks; and
e. performing a prediction for the RR interval for the best group; and
f. if the prediction doesn't fit the real physiological model of the fetal RR intervals, the current signal is ignored and one then begins the process at the beginning (i.e. using a moving window to calculate the relation) with the next signal; and
g. if the prediction does fit the real physiological model of the fetal RR, calculate the auto correlation function of a windowed RMS of the signal. If the result has a narrow distribution, the current signal is ignored, and if the result does not have a narrow distribution, then proceed as follows:
h. applying AGC to the negative derivative signal; and
i. normalizing the result.

In certain embodiments, the above 'peak-2-mean transformation' is applied separately to each signal (i.e. each of the 2N signals or each of the between N+1 and less than 2N signals).

In some embodiments, fetal heart beat detection is performed. For example, in some embodiments, the N raw fetal signal data are subjected the fetal peak detection procedure before the further analysis and in other embodiments the results of the further analysis subjected to the fetal peak detection procedure.

In some embodiments, the analysis comprises: dividing the N filtered fetal signal data into segments; normalizing the signal data in each segment; calculating the first derivative of the normalized signal data; identifying the fetal ECG peaks within the normalized signal data by determining the zero-crossing of the first derivative; excluding peaks whose absolute value is less than a threshold pre-selected by the user; and excluding very close peaks where the distance between them is less than a threshold, thereby obtaining processed N filtered fetal signal data.

In some embodiments, the length of each segment is set at 10 seconds.

In some embodiments, the length of each segment is selected automatically depending on the length of the recording.

In some embodiments, the signal data in each segment is normalized by the absolute maximum value of the signal data. In some embodiments, the signal data in each segment is normalized by the absolute non-zero minimum value of the signal data.

In some embodiments, a first order forward derivative is used. In some embodiments, a first order central derivative is used.

In some embodiments, the threshold is selected to be a constant value of 0.3.

In some embodiments, the threshold is selected depending on the local characteristics of the signal data. In some embodiments, the local characteristic of the signal is the median value of the signal data or any multiplication of this value. In some embodiments, the local characteristic of the signal is the mean value of the signal data or any multiplication of this value.

In some embodiments, the threshold on the distance is selected to be 100 samples.

In some embodiments, the local characteristics of the signal can be the maximum predicted RR internal or any multiple of this value.

In some embodiments, a "peaks array" is generated from the filtered N-ECG fetal signals data. In some embodiments, the peak array comprises the number of detected peaks for each of the segments of the filtered N-ECG fetal signals data.

In some embodiments, clustering is performed on the peaks array. In some embodiments, k-means clustering is used to group the peaks into a number of clusters. In some embodiments, k-medoids clustering is used to group the peaks into a number of clusters.

In some embodiments, the number of clusters for the clustering is set to be three. In some embodiments, the number of clusters for the clustering is selected automatically depending on the characteristics of the filtered N-ECG fetal signals data.

In some embodiments, the clustering is used to exclude outliers. In some embodiments, outliers are peaks that have anomalous characteristics.

In some embodiments, the characteristic is the distance between a peak and its neighboring peaks. In some embodiments, the characteristic is the amplitude of the peak.

In some embodiments, a new peak array is constructed after the exclusion of the anomalous peaks.

In some embodiments, the new peak array is further analyzed and the peaks are scored depending on the signal to noise ratio of the filtered N-ECG fetal signals data.

In some embodiments, the signal to noise ratio score is calculated by calculating the relative energy of the QRS complexes from the overall energy of the filtered N-ECG fetal signals data.

In some embodiments, the detected peaks for each of the filtered N-ECG fetal signals data are fused for a more robust detection. In some embodiments, the fusion of the detected peaks is done using the scores given for each of the peaks of filtered N-ECG fetal signals data.

In some embodiments, a global array of peaks is defined using the fused peaks.

In some embodiments, the peaks of each of the filtered N-ECG fetal signals data is redetected and the positions are refined using the global peaks array. In some embodiments, the global peak array is constructed based on the best lead with corrections made using the peaks from the other leads and the global peaks array is examined using physiological measures, such as, for example, RR intervals, HR, HRV).

In some embodiments, the beat-to-beat fetal heart rate is extracted from the detected fetal peaks positions. In some embodiments, the fetal heart curve is also extracted from the detected fetal peak positions.

The present invention is further illustrated, but not limited by, the following examples.

EXAMPLES

Example 1: Algorithm Design According to Some Embodiments of the Present Invention

TABLE 1

5. Low Level Design of the algorithm: The fECG detection algorithm have the following low level design:
  5.1. The acquired N-channels signals should be preprocessed:
    5.1.1. Signal exclusion: Saturated signals are excluded in this version (if the saturated part exceeds 10% of the overall length of the signal). For the next versions, this criterion should be replaced by an online examiner.
    5.1.2. Baseline removal: the baseline of the ECG signal needs to be removed. It can be removed using a number of methods. In the algorithm the baseline is removed using a moving average filter with an order of 501 (milliseconds).
    5.1.3. Low pass filtering with an IIR filter (auto designed by Matlab):
      5.1.3.1. Type: Chebyshev Type I
      5.1.3.2. Cutoff freq: 70 Hz
      5.1.3.3. Baseband ripple: 0.12 dB
      5.1.3.4. Order: 12th order, 6 sections
    5.1.4. Power line interference cancelation: to be in the safe side and for simplicity purposes, the following filter is used:
      5.1.4.1. Type: Butterworth (band-stop)
      5.1.4.2. Cutoff freq: 49.5-50.5 Hz
      5.1.4.3. Order: 10th order, 5 sections
  5.2. Maternal ECG detection: The following steps are performed:
    5.2.1. Examination: the data is passed through an additional high pass filter (5th order @1 Hz). The data is examined by preliminary and simple peak detector. The relative energy of the peaks is calculated (relative to the overall energy of the signal). Each signal is given a quality score depending on this measure. Signals with a quality score of less than a threshold are excluded. In addition, the signals are examined for missing data and NaNs.
    5.2.2. Peak enhancement: The preprocessed ECG data is passed through an additional median filter with an order of 100 samples to enhance the maternal peaks.
    5.2.3. Peaks detection: for each signal:
      5.2.3.1. Divide the signal into 10 seconds segments, for each segment:

TABLE 2

5.2.3.2. Normalize the data
      5.2.3.3. Find the local peaks in the segment using derivative, thresholding and minimum distances methods
      5.2.3.4. After finishing with all of the segments perform kmedoids clustering on the number of peaks in each segments:
        5.2.3.4.1. For segments with very low number of peaks, (apparently there is a noise spike) perform AGC on the data and redetect the peaks. If the new number of peaks belongs to one of the good clusters, add these peaks. If not, ignore these peaks
        5.2.3.4.2. For segments with very high number of peaks (due to high noise most probably), ignore these peaks
      5.2.3.5. After finishing, perform kmedoids clustering on the amplitudes of the peaks, very low peaks and very high peaks are filtered using this step.
      5.2.3.6. After finishing with the signal, do the following:
        5.2.3.6.1. Check that the number of peaks falls into an expected interval (based on the maximum and minimum possible heart rates)
        5.2.3.6.2. Is step 1 is passed, check that the relative energy of the QRS complexes is higher than a threshold
        5.2.3.6.3. If step 2 is passed, perform peak redetection using the cross correlation method (helps removing false positive and adding false negatives)
    5.2.4. Peak re-detection: if the previous step is failed to detect the peaks in at least one channel, apply ICA to the data and then repeat step (5.2.3)
    5.2.5. Peaks examination:
      5.2.5.1. A score is given for each one of the N signals. The best lead is defined as the lead with the biggest score
      5.2.5.2. A global peak array is constructed based on the best lead with corrections made using the peaks from the other leads

TABLE 3

5.5.5.3. The global peaks array is examined using physiological measures (RR intervals, HR, HRV)
5.2.6. HRC calculation: the mHRC is calculated using the detected maternal R-waves
5.3. Maternal ECG Elimination: The purpose of this step is to eliminate the maternal ECG and thereafter stay with the fetal ECG signals and some noise according to the model that have been previously developed. The following steps are performed for each of the N-channels:
    5.3.1. Resample the signal to match a 4kSPS sampling frequency
    5.3.2. Find the QRS onset and offset positions using the Curve Length Transform (CLT)
    5.3.3. For each one of the detected maternal peaks:
        5.3.3.1. Define a beat interval: the beat interval is defined as, except for the first and last peaks, (1) beat onset: half the distance between the current peak and the previous peak and (2) beat offset: half the distance between the current peak and the next peak. Due to the beat-2-beat changing heart rate, the beat interval should change for each beat
        5.3.3.2. Define a local template, a template that depends on the current beat:
            5.3.3.2.1. Step 1: Search for at least 10 beats that have a correlation coefficient (obtained from cross correlation) of at least 0.98 This step is usually fast and gives results for not-noisy signals
            5.3.3.2.2. Step 2: Step 1 usually fails for noisy signals hence an iterative scheme is used:
                5.3.3.2.2.1. Define the template as the beat itself
                5.3.3.2.2.2. An initial correlation coefficient is defined (high value threshold: 0.99)
                5.3.3.2.2.3. Search for the beats that are very similar to the current beat (have higher correlation than the threshold)
                5.3.3.2.2.4. If none is found, decrease the correlation threshold and repeat

TABLE 4

5.3.3.2.2.5. If some is found, update the template and continue
                5.3.3.2.2.6. The procedure is terminated if: (1) a maximum number of iterations is reached, (2) the number of beats to include reached a minimum number or (3) the current iteration yields the same results as the previous iteration
            5.3.3.2.3. A byproduct of this process is a score for how noisy each beat is
    5.3.4. Start the adaptation procedure, iterative Levenberg-Marquardt Parametric Optimization (LMPO) for solving non-linear damped least squares problems. Divide the beat into 3 parts: (1) P-wave region, (2) QRS complex and (3) T-wave region. The iterative procedure:
        5.3.4.1. Initialize the LMA algorithm (Algorithm params)
        5.3.4.2. Perform initial guess for the mECG (first guess is the template, let it be $\phi\_c$)
        5.3.4.3. Adapt the initial guess
        5.3.4.4. Compare the result to the measured current ECG (current beat with maternal data, fetal data and noise, let it be $\phi\_m$)
        5.3.4.5. Check if a termination criteria is reached, if yes terminate returning the last good result
        5.3.4.6. If not, update the algorithm parameters and repeat steps 3-5.
        5.3.4.7. This algorithm has the following characteristics:
It interpolates between Gauss - Newton (GN) method and the Gradient Decent (GD) method taking the good form both
At first, it convergence very fast due to the fast convergence of GD. When it advances, the steps become smaller, yielding a slow convergence when it is close to the local minimum (Slow yet cautious progress near the minimum!)

TABLE 5

It operates by the principle of "worst case scenario is to stay the same"

The only problem with this iterative algorithm is the convergence to local minima. This isn't a big issue in our case since we know that the local minima is also, always, the global one (due to the educated guess of the start conditions)

The algorithm minimizes the error energy function defined as the l2 norm of the difference between the calculated potentials and the measured potentials: $E = \|\phi_c - \phi_m\|^2$ The final result of the algorithm is a stable, global and reproducible solution due to the fact the number of parameters to be reconstructed is way smaller than the number of the available observations The reconstruction parameters of the algorithm are:

P region multiplier

QRS region multiplier

T region multiplier

Beat shift

TABLE 6

| | | |
|---|---|---|
| | 5.3.5. | Construct the maternal ECG (mECG) array (started form the templates for each beat and get close to the current channel measured ECG) |
| | 5.3.6. | Construct the fetal ECG array, fECG = ECG-mECG |
| | 5.3.7. | Downsample the mECG and the fECG signals to match the initial sampling rate |
| 5.4. | | Fetal ECG preprocessing: After the elimination (near-perfect elimination) of the mECG, the remaining data is processed for fECG enhancement (see the next step for more info). A preliminary prediction of the best fetal channel is performed depending on the energy distribution of the auto correlation function of the signal |
| 5.5. | | Fetal ECG detection: |
| | 5.5.1. | First step is to prepare the data. Usually, the fetal signals do not appear in all of the channels hence it is better to decrease the dimension of the data. This is done by: |
| | 5.5.2. | Apply Singular Value Decomposition (SVD) keeping only the N − 1 singular values and vectors |
| | 5.5.3. | Apply fastICA to the resulting data (with 'tanh') |
| | 5.5.4. | Apply peak-2-mean transformation: |
| | | 5.5.4.1. Use a moving window to calculate the relation: max(signal[win])/mean(signal[win]) (enhances peaks) |
| | | 5.5.4.2. Calculate the 1st derivative of the result of step 1 |
| | | 5.5.4.3. Find the zero crossing to find peaks, take the negative part of the derivative |
| | | 5.5.4.4. Find the peaks in the previous result and cluster them based on the difference between them. Identify the best group as the group with the maximum score: SCR = n/RMS where n is the number of peaks in each cluster and RMS is the energy of the derivative of the distance between the peaks |
| | | 5.5.4.5. Perform a prediction for the RR interval for the best group |
| | | 5.5.4.6. If the prediction doesn't fit the real model, ignore this channel |

TABLE 7

| | | |
|---|---|---|
| | 5.5.4.7. | If so, calculate the auto correlation function of a windowed RMS of the signal, if the result have a narrow distribution ignore this channel, else: |
| | 5.5.4.8. | Apply AGC to the negative derivative signal |
| | 5.5.4.9. | Normalize the result, and flag it as the processing data |
| | 5.5.4.10. | Repeat steps 1-10 to the N-channels |
| 5.5.5. | | Try to perform fetal peak detection using the same methodology as for the maternal peak detection with different parameters |
| 5.5.6. | | If the previous step is successful, skip this step. If not, this means that the fetal data is noisy. In this case perform the following preprocessing: |
| | 5.5.6.1. | The fetal data is band-pass filtered between the range 15-70 Hz |
| | 5.5.6.2. | Wavelet denoising is applied to the data |
| | 5.5.6.3. | Windowed RMS is applied on the data |
| | 5.5.6.4. | The results are low pass filtered @35 Hz |
| | 5.5.6.5. | The data is normalized and AGC is applied to the data |
| 5.5.7. | | Following step (5.5.6), perform fetal peak detection without the correlation part |
| 5.5.8. | | Following step (5.5.7), if more than one channel is valid, calculate the kurtosis of the distribution of the distances between the peaks. The best lead is defined as the peak with the maximum relative kurtosis |
| 5.5.9. | | Following step (5.5.8), perform peak redetection using the RR intervals. Also try to build, using a Kalman filter, an array of the positions of the peaks |
| 5.5.10. | | Following step (5.5.5/5.5.9), perform fetal peak examination using the information about the RR intervals |
| 5.5.11. | | Following step (5.5.10), build the fetal peaks array: |
| | 5.5.11.1. | Time varying RR interval is extracted from the results |
| | 5.5.11.2. | A characteristic region in the previous signal is defined: a region in which the RR interval curve is very smooth (which means that there is minimum falses in this region) - this region is called the seed region |
| | 5.5.11.3. | Perform region growing staring from the seed points while including only points that are close to the local RR interval |

TABLE 8

| | | |
|---|---|---|
| | 5.5.12. | Perform peak examination and correction: |
| | | 5.5.12.1. Stage 1: find false negatives and Zigzags (caused by two consecutive, opposite misdetections) |
| | | 5.5.12.2. Stage 2: Find mis-positioning of the peaks by detecting spikes in the updating RR curve |
| 5.6. | | HRC calculation: the fHRC is calculated using the detected fetal peaks |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A computer-implemented method,
wherein the method determines the health of a fetus,
wherein the method comprises:
receiving, by at least one computer processor executing specific programmable instructions configured for the method, raw Electrocardiogram (ECG) signals data from at least one pair of ECG sensors;
wherein the at least one pair of ECG sensors are positioned on an abdomen of a woman carrying a fetus;
wherein the raw ECG signals data comprise data representative of a plurality of raw ECG signals which are being acquired in real-time from the at least one pair of ECG sensors;

detecting, by the at least one computer processor, maternal heart peaks in each of the ECG signals in the ECG signals data;
subtracting, by the at least one computer processor, from each of the plurality of ECG signals of the ECG signals data, a maternal ECG signal, by utilizing at least one non-linear subtraction procedure to obtain corrected ECG signals data which comprise data representative of a plurality of corrected ECG signals, each of the plurality of corrected ECG signals corresponding to one of the ECG signals, wherein the at least one non-linear subtraction procedure comprises:
  iteratively performing:
    i) dividing each of the plurality of ECG signals into a plurality of ECG signal segments,
      1) wherein each ECG signal segment of the plurality of ECG signal segments corresponds to a beat interval of a full heartbeat, and
      2) wherein each beat interval is automatically determined based, at least in part, on detecting an onset value and an offset value of the respective beat interval;
    ii) modifying each of the plurality of ECG signal segments to form a plurality of modified ECG signal segments, wherein the modifying is performed using at least one inverse optimization scheme based on a set of parameters, wherein values of the set of parameters are determined based on:
      iteratively performing:
        1) defining a global template based on a standard heartbeat profile of an adult human being,
        2) setting a set of tentative values for a local template for each of the ECG signal segments,
        3) utilizing at least one optimization scheme to determine an adaptive template for each of the ECG signal segments based on the local template being matched to the global template within a pre-determined similarity value; and
    iii) eliminating each of the modified ECG signal segments from the corresponding one of the ECG signals, by subtracting the adaptive template from the one of the ECG signals thereby generating each corrected ECG signal;
extracting, by the at least one computer processor, fetal ECG signals data from the ECG signals data based on the corrected ECG signals data, wherein the fetal ECG signals data comprises a plurality of fetal ECG signals, each of the fetal ECG signals corresponding to one of the ECG signals;
detecting, by the at least one computer processor, fetal heart peaks in the fetal ECG signals data;
calculating, by the at least one computer processor, based on the detected fetal heart peaks, at least one of:
  i) a fetal heart rate,
  ii) a fetal heart curve,
  iii) a beat-2-beat fetal heart rate, and
  iv) fetal heart rate variability; and
outputting, by the at least one computer processor, a result of the calculating step, wherein the result of the calculating step is used to determine the health of the fetus.
2. The method of claim 1, further comprising:
digital signal filtering, by the at least one computer processor, the plurality of raw ECG signals to form filtered ECG signals data having a plurality of filtered ECG signals, wherein the step of detecting maternal heart peaks is performed on the filtered ECG signals in the filtered ECG signals data,
wherein the digital signal filtering utilizes at least one of:
  i) a baseline wander filtering,
  ii) a power line frequency filtering,
  iii) a high frequency filtering, and
  iv) a digital adaptive inverse-median filtering, and
wherein the detecting of the maternal heart peaks is performed on the filtered ECG signals data.
3. The method of claim 2, wherein the filtered ECG signals data is data which, prior to the detecting the maternal peaks in the filtered ECG signals data, has been processed with at least one decomposition technique, wherein the at least one decomposition technique is selected from the group consisting of:
  a. Singular-Value-Decomposition (SVD),
  b. Principal-Component-Analysis (PCA),
  c. Independent-Component-Analysis (ICA),
  d. Wavelet-Decomposition (CWT), and
  e. any combination thereof.
4. The method of claim 1, wherein the detecting of the maternal heart peaks in each ECG signal in the ECG signals data is performed based at least on:
  i) dividing each ECG signal into a first plurality of ECG signal segments;
  ii) normalizing an ECG signal in each ECG signal segment;
  iii) calculating a first derivative of the ECG signal in each ECG signal segment;
  iv) finding local maternal heart peaks in each ECG signal segment based on determining a zero-crossing of the first derivative; and
  v) excluding the local maternal heart peaks having at least one of:
    1) an absolute value which is less than a pre-determined local peak absolute threshold value; and
    2) a distance between the local peaks is less than a pre-determined local peak distance threshold value.
5. The method of claim 1, wherein the pre-determined similarity value is based on an Euclidian distance, wherein the set of parameters is a local minima solution to a non-linear least squares problem solved by at least one of:
  1) minimizing a cost function taken as the Euclidian distance;
  2) utilizing a Gauss-Newton algorithm;
  3) utilizing a Steepest-Descent (Gradient-Descent) algorithm; and
  4) utilizing a Levenberg-Marquardt algorithm.
6. The method of claim 1, further comprising:
processing, by the at least one computer processor, the fetal ECG signals data to improve a signal-to-noise ratio of the fetal ECG signals, thereby forming filtered fetal ECG signals data,
wherein the processing of the fetal ECG signals data to improve the signal-to-noise ratio comprises:
  i) applying a band-pass filter within a range of 15-65 Hz to break the plurality of fetal ECG signals in to a plurality of frequency filtered channels,
  ii) scoring a fetal ECG signal per channel based on a peak-2-mean analysis to identify a plurality of fetal heartbeat channels, wherein each fetal heartbeat channel corresponds to a particular fetal ECG signal; and
  iii) selecting the identified plurality of fetal heartbeat channels into filtered fetal ECG signals data, comprising a plurality of filtered fetal ECG signals, each of the filtered fetal ECG signals corresponding to one of the fetal ECG signals.

7. The method of claim 6, wherein the processing of the raw fetal ECG signals data to improve the signal-to-noise ratio further comprises at least one of:
   1) utilizing a Singular-Value-Decomposition (SVD) technique; and
   2) utilizing a Wavelet-Denoising (WD) technique.

8. A computer-implemented method,
   wherein the method determines the health of a fetus,
   wherein the method comprises:
   receiving, by at least one computer processor executing specific programmable instructions configured for the method, raw Electrocardiogram (ECG) signals data from at least one pair of ECG sensors;
      wherein the at least one pair of ECG sensors are positioned on an abdomen of a woman carrying a fetus;
      wherein the ECG signals data comprise data representative of a plurality of ECG signals which are being acquired in real-time from the at least one pair of ECG sensors;
   detecting, by the at least one computer processor, maternal heart peaks in each ECG signal in the ECG signals data, by performing at least:
      i) dividing each ECG signal into a first plurality of ECG signal segments;
      ii) normalizing an ECG signal in each ECG signal segment;
      iii) calculating a first derivative of the ECG signal in each ECG signal segment;
      iv) finding local maternal heart peaks in each ECG signal segment based on determining a zero-crossing of the first derivative; and
      v) excluding the local maternal heart peaks having at least one of:
         1) an absolute value which is less than a pre-determined local peak absolute threshold value; and
         2) a distance between the local peaks is less than a pre-determined local peak distance threshold value;
   subtracting, by the at least one computer processor, from each ECG signal of the ECG signals data, the maternal ECG signal, by utilizing at least one non-linear subtraction procedure to obtain corrected ECG signals data which comprise data representative of a plurality of corrected ECG signals, each of the corrected ECG signals corresponding to one of the ECG signals,
      wherein the at least one non-linear subtraction procedure comprises:
      iteratively performing:
         i) automatically dividing each ECG signal of ECG signals data into a second plurality of ECG signal segments,
            1) wherein each ECG signal segment of the second plurality of ECG signal segments corresponds to a beat interval of a full heartbeat;
            2) wherein each beat interval is automatically determined based, at least in part, on automatically detecting an onset value and an offset value of the respective beat interval, and
            3) wherein the automatically detecting of the onset value and the offset value of each beat interval is based, at least in part, on:
               a) a number of maternal peaks detected in each ECG signal,
               b) changing a sample rate of each ECG signal by an integer number,
               c) an onset of each P-wave,
               d) an offset of each T-wave, and
               e) in-beat segmentation;
         ii) automatically modifying each of the second plurality of ECG signal segments to form a plurality of modified ECG signal segments, wherein the modifying is performed using at least one inverse optimization scheme based on a set of parameters, wherein values of the set of parameters are determined based on:
            iteratively performing:
               1) defining a global template based on a standard heartbeat profile of an adult human being;
               2) setting a set of tentative values for a local template for each ECG signal segment; and
               3) utilizing at least one optimization scheme to determine an adaptive template for each ECG signal segment based on the local template being matched to the global template within a pre-determined similarity value; and
         iii) automatically eliminating the modified segments from each the ECG signals, by subtracting the adaptive template from each ECG signal thereby generating each corrected ECG signal, thereby generating corrected ECG signals data;
   extracting, by the at least one computer processor, raw fetal ECG signals data, by utilizing a Blind-Source-Separation (BSS) algorithm on (1) the ECG signals data and (2) the corrected ECG signals data, wherein the raw fetal ECG signals data comprises a plurality of fetal ECG signals, each of the plurality of fetal ECG signals corresponding to one of the ECG signals;
   detecting, by the at least one computer processor, fetal heart peaks in the fetal ECG signals data, by performing at least:
      i) dividing each fetal ECG signal into a first plurality of fetal ECG signal segments;
      ii) normalizing a fetal ECG signal in each fetal ECG signal segment;
      iii) calculating a first derivative of the fetal ECG signal in each fetal ECG signal segment; and
      iv) finding local fetal heart peaks in each fetal ECG signal segment based on determining a zero-crossing of the first derivative;
   calculating, by the at least one computer processor, based on detected fetal heart peaks, at least one of:
      i) a fetal heart rate,
      ii) a fetal heart curve,
      iii) a beat-2-beat fetal heart rate, and
      iv) fetal heart rate variability; and
   outputting, by the at least one computer processor, a result of the calculating step, wherein the result of the calculating step is used to determine the health of the fetus.

9. The method of claim 8, further comprising:
   digital signal filtering, by the at least one computer processor, the ECG signals data to form filtered ECG signals data having a plurality of filtered ECG signals, each of the plurality of the filtered ECG signals corresponding to one of the ECG signals of the ECG signals data,
   wherein the step of detecting maternal heart peaks is performed on the plurality of filtered ECG signals of the filtered ECG signals data, wherein the digital signal filtering utilizes baseline wander filtering, and
wherein the baseline wander filtering comprises utilizing at least one of:
1) a moving average filter having constant weights, and
2) a moving median filter.

10. The method of claim 8, further comprising:
digital signal filtering, by the at least one computer processor, the ECG signals data to form filtered ECG signals data having a plurality of filtered ECG signals, each of the plurality of the filtered ECG signals corresponding to one of the ECG signals of the ECG signals data,
wherein the step of detecting maternal heart peaks is performed on the plurality of filtered ECG signals of the filtered ECG signals data,
wherein the digital signal filtering utilizes power line frequency filtering, and
wherein the power line frequency filtering comprises utilizing at least one of:
1) a band-stop digital filter; and
2) a digital adaptive filter.

11. The method of claim 8, further comprising:
digital signal filtering, by the at least one computer processor, the ECG signals data to form filtered ECG signals data having a plurality of filtered ECG signals, each of the plurality of the filtered ECG signals corresponding to one of the ECG signals of the ECG signals data,
wherein the step of detecting maternal heart peaks is performed on the plurality of filtered ECG signals of the filtered ECG signals data,
wherein the digital signal filtering utilizes high frequency filtering, and
wherein the high frequency filtering comprises utilizing at least one of:
1) a digital low pass filter;
2) a cutoff frequency of at least 70 cycles per second;
3) a smoothing filter; and
4) an edge-preserving filter.

12. The method of claim 11, wherein the edge-preserving filter is one of:
a. an adaptive mean filter; and
b. an adaptive median filter.

13. The method of claim 8, further comprising:
digital signal filtering, by the at least one computer processor, the ECG signals data to form filtered ECG signals data having a plurality of filtered ECG signals, each of the plurality of the filtered ECG signals corresponding to one of the ECG signals of the ECG signals data,
wherein the step of detecting maternal heart peaks is performed on the plurality of filtered ECG signals of the filtered ECG signals data,
wherein the digital signal filtering utilizes digital adaptive inverse-median filtering, and
wherein the digital adaptive inverse-median filtering comprises utilizing an adaptive median filter, having a length to be either:
1) a constant value, or
2) adapted depending on at least one local characteristic of the ECG signals data.

14. The method of claim 13, wherein the at least one local characteristic is a duration of at least one of:

a. a QRS complex;
b. a ST segment; and
c. a PR interval.

15. The method of claim 8, further comprising:
prior to the detecting the maternal peaks in the ECG signals data, processing the ECG signals data with at least one decomposition technique, wherein the at least one decomposition technique is selected from the group consisting of:
a. Singular-Value-Decomposition (SVD);
b. Principal-Component-Analysis (PCA);
c. Independent-Component-Analysis (ICA);
d. Wavelet-Decomposition (CWT), and
e. any combination thereof.

16. The method of claim 8, wherein the pre-determined similarity value is based on an Euclidian distance, wherein the set of parameters is a local minima solution to a non-linear least squares problem solved by at least one of:
1) minimizing a cost function taken as the Euclidian distance;
2) utilizing a Gauss-Newton algorithm;
3) utilizing a Steepest-Descent (Gradient-Descent) algorithm; and
4) utilizing a Levenberg-Marquardt algorithm.

17. The method of claim 8, further comprising:
processing, by the at least one computer processor, the fetal ECG signals data to improve a signal-to-noise ratio thereof by at least:
i) applying a band-pass filter within a range of 15-65 Hz to break the plurality of fetal ECG signals into a plurality of frequency channels,
ii) scoring a fetal ECG signal per channel based on a peak-2-mean analysis to identify a plurality of fetal heartbeat channels, wherein each fetal heartbeat channel corresponds to one of the fetal ECG signals; and
iii) selecting the identified plurality of fetal heartbeat channels into filtered fetal ECG signals data, the filtered ECG signals data comprising a plurality of filtered fetal ECG signals, each of the plurality of filtered fetal ECG signals corresponding to one of the fetal ECG signals;
wherein the processing of the fetal ECG signals data to improve the signal-to-noise ratio further comprises at least one of:
1) utilizing a Singular-Value-Decomposition (SVD) technique; and
2) utilizing a Wavelet-Denoising (WD) technique.

18. The method of claim 8, wherein the at least one pair of ECG sensors is selected from the group consisting of: at least one of a wet contact ECG electrode; and at least one dry contact ECG electrode.

19. The method of claim 8, wherein a number of in-beat segments in the in-beat segmentation is based on utilizing at least one of the following:
1) a Divide and Conquer algorithm; and
2) a digital band pass filter.

20. The method of claim 8, wherein a number of in-beat segments in the in-beat segmentation is three, the three beats being defined as follows:
1) a first in-beat segment defined from the onset value of a particular beat interval to an onset of a QRS complex;
2) a second in-beat segment defined to be the QRS complex; and
3) a third in-beat segment defined from an offset of the QRS complex to the offset value of the particular beat interval.

* * * * *